(12) United States Patent
Wraith et al.

(10) Patent No.: US 11,542,316 B2
(45) Date of Patent: Jan. 3, 2023

(54) S-ARRESTIN PEPTIDES AND THERAPEUTIC USES THEREOF

(71) Applicant: APITOPE INTERNATIONAL NV, Diepenbeek (BE)

(72) Inventors: David Wraith, Chepstow (GB); Evelien Schurgers, Chepstow (GB); Keith Martin, Chepstow (GB); Liselotte Jansson, Chepstow (GB)

(73) Assignee: Worg Pharmaceuticals (Zhejiang) Co., Ltd., Zhejiang (CN)

( * ) Notice: Subject to any disclaimer, the term of this patent is extended or adjusted under 35 U.S.C. 154(b) by 139 days.

(21) Appl. No.: 16/474,590

(22) PCT Filed: Jan. 4, 2018

(86) PCT No.: PCT/IB2018/050063
§ 371 (c)(1),
(2) Date: Jun. 28, 2019

(87) PCT Pub. No.: WO2018/127830
PCT Pub. Date: Jul. 12, 2018

(65) Prior Publication Data
US 2019/0330298 A1    Oct. 31, 2019

(30) Foreign Application Priority Data
Jan. 4, 2017    (GB) .................................... 1700104

(51) Int. Cl.
*C07K 14/705*    (2006.01)
*A61K 38/00*    (2006.01)
*A61P 37/06*    (2006.01)
*A61P 27/02*    (2006.01)
*A61P 25/02*    (2006.01)

(52) U.S. Cl.
CPC ............ *C07K 14/705* (2013.01); *A61P 25/02* (2018.01); *A61P 27/02* (2018.01); *A61P 37/06* (2018.01); *A61K 38/00* (2013.01)

(58) Field of Classification Search
None
See application file for complete search history.

(56) References Cited

U.S. PATENT DOCUMENTS

| | | |
|---|---|---|
| 6,790,447 B1 | 9/2004 | Wildner et al. |
| 2012/0276127 A1* | 11/2012 | Adamus ............ A61K 39/0005 424/185.1 |
| 2012/0276155 A1* | 11/2012 | Kishimoto ............ A61K 39/00 424/400 |
| 2013/0058975 A1 | 3/2013 | Maldonado et al. |
| 2014/0322188 A1 | 10/2014 | Nussenblatt et al. |

FOREIGN PATENT DOCUMENTS

| | | | | |
|---|---|---|---|---|
| JP | 2016501850 A | 1/2016 | | |
| JP | 2016527324 A | 9/2016 | | |
| WO | WO-0157275 A2 * | 8/2001 | ............. | C07K 14/47 |
| WO | WO-02/16410 A2 | 2/2002 | | |
| WO | WO-2008001380 A2 * | 1/2008 | ............. | A61P 37/04 |
| WO | WO-2014/072958 A1 | 5/2014 | | |
| WO | WO-2014/077825 A1 | 5/2014 | | |
| WO | WO-2015/023504 A1 | 2/2015 | | |

OTHER PUBLICATIONS

Pennesi et al (J Clin Invest 111: 1171-1180, 2003).*
Akdis et al., Role of interleukin 10 in specific immunotherapy, J. Clin. Invest., 102:98-106 (1998).
Altschul et al., Gapped BLAST and PSI-BLAST: a new generation of protein database search programs, Nucleic Acids Res. 25:3389-402 (1997).
Anderton et al., Hierarchy in the ability of T cell epitopes to induce peripheral tolerance to antigens from myelin, Eur. J. Immunol., 28:1251-61 (1998).
Anderton et al., Mechanisms of central and peripheral T-cell tolerance: lessons from experimental models of multiple sclerosis, Immunol. Rev., 169:123-37 (1999).
Burton et al., Sequential transcriptional changes dictate safe and effective antigen-specific immunotherapy, Nat. Commun., 5:4741 (Sep. 2014).
Fukushima et al., Human lymphocyte responses against epitopes of a self antigen: a follow-up at different time points, Cell Immunol., 167(1):150-3 (Jan. 1996).
Fukushima et al., Permissive recognition of immunodominant determinants of the retinal S-antigen in different rat strains, primates and humans, Int. Immunol., 9(1):169-77, 1996.
Holm et al., Touring protein fold space with Dali/FSSP, Nucleic Acid Res., 26:316-9 (1998).
Holm, Dali: a network tool for protein structure comparison, Trends Biochem. Sci., 20:478-80 (1995).
Holm, Protein structure comparison by alignment of distance matrices, J. Mol. Biol., 233:123-38 (1993).
International Application No. PCT/IB2018/050063, International Search Report and Written Opinion, dated May 2, 2018.
Liu et al., Affinity for class II MHC determines the extent to which soluble peptides tolerize autoreactive T cells in naive and primed adult mice—implications for autoimmunity, Int. Immunol., 7:1255-63 (1995).
Mattapallil et al., Uveitis-associated epitopes of retinal antigens are pathogenic in the humanized mouse model of uveitis and identify autoaggressive T cells, J. Immunol., 187(4):1977-85 (Aug. 2011).
Metzler et al., Inhibition of experimental autoimmune encephalomyelitis by inhalation but not oral administration of the encephalitogenic peptide: influence of MHC binding affinity, Int. Immunol., 5:1159-65 (1993).

(Continued)

*Primary Examiner* — Gregory S Emch
*Assistant Examiner* — Aditi Dutt
(74) *Attorney, Agent, or Firm* — Marshall, Gerstein & Borun LLP

(57) ABSTRACT

The present invention relates to a composition which comprises peptides derived from S-Arrestin (retinal arrestin, S-antigen, S-Ag). The composition or peptides may be useful in the prevention and/or suppression of S-Ag autoimmunity, which is useful in the treatment and/or prevention of uveitis.

12 Claims, 19 Drawing Sheets

Figure 1:
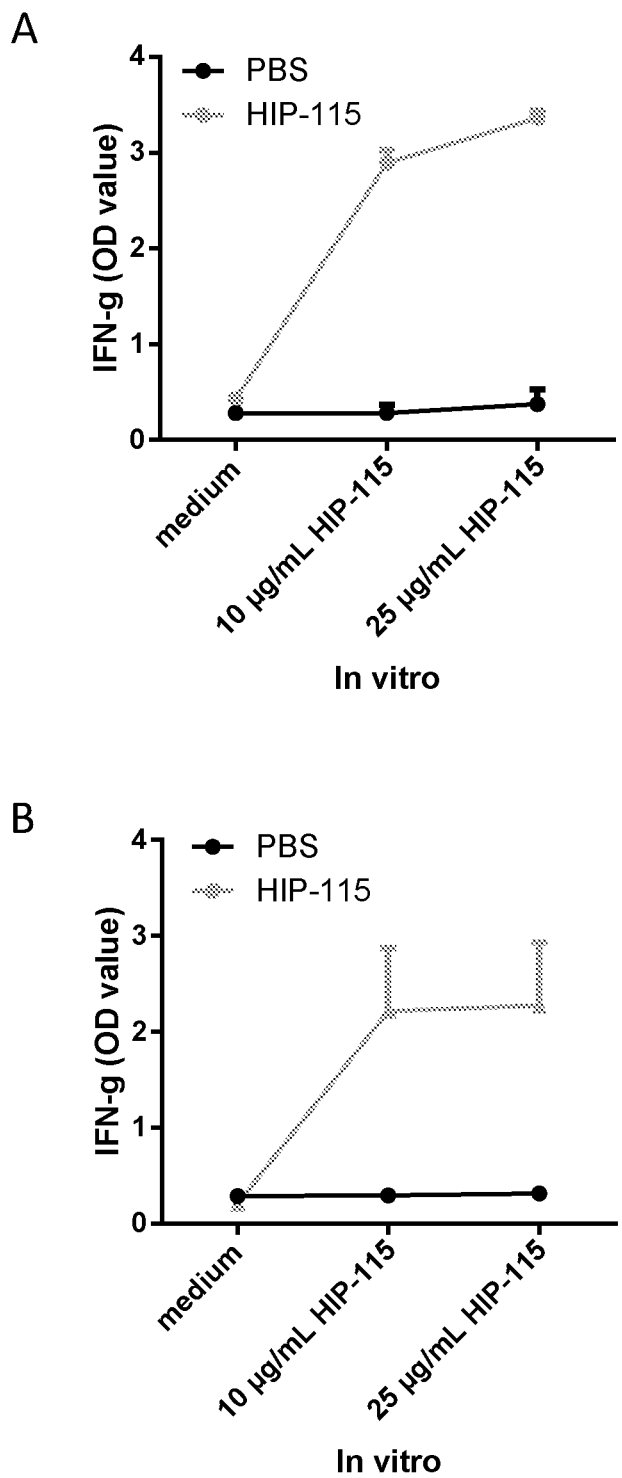

Specification includes a Sequence Listing.

(56) References Cited

OTHER PUBLICATIONS

Muller et al., Successful immunotherapy with T-cell epitope peptides of bee venom phospholipase A2 induces specific T-cell anergy in patients allergic to bee venom, J. Allergy Clin Immunol., 101:747-54 (1998).

Myers et al., Optical alignments in linear space, CABIOS, 4(1):11-7 (1988).

Nielsen et al., NetMHCIIpan-2.0—Improved pan-specific HLA-DR predictions using a novel concurrent alignment and weight optimization training procedure, Immunome Res., 6:9 (2010).

Nielsen et al., NN-align. An artificial neural network-based alignment algorithm for MHC class II peptide binding prediction, BMC Bioinformatics, 10:296 (Sep. 2009).

Pearson et al., Improved tools for biological sequence comparison, *Proc. Natl. Acad. Sci.* 85:2444-8 (1988).

Pearson, Rapid and sensitive sequence comparison with FASTP and FASTA, *Methods Enzymol.* 183:63-98 (1990).

Roberge et al., A strategy for a convergent synthesis of N-linked glycopeptides on a solid support, Science, 269:202-4 (1995).

Thompson et al., CLUSTAL W: improving the sensitivity of progressive multiple sequence alignment through sequence weighting, position-specific gap penalties and weight matrix choice, Nucleic Acids Res. 22:4673-80 (1994).

Thurau et al., Induction of oral tolerance to S-antigen induced experimental autoimmune uveitis by a uveitogenic 20mer peptide, J. Autoimmun., 4(3):507-16 (Jun. 1991).

Wraith et al., Autoimmunity: Antigen-specific immunotherapy, Nature, 530(7591):422-3 (Feb. 2016).

Bodanszky, Peptide Chemistry: A Practical Textbook, Springer-Verlag Berlin (1988).

Creighton, Proteins Structures And Molecular Principles, New York NY: WH Freeman and Co. (1983).

Gennaro, Remington: The Science and Practice of Pharmacy, 20th edition, Lippincott, Williams, & Wilkins (2000).

Global Data On Visual Impairments 2010, The World Health Report, World Health Organization, downloaded from the Internet at:<http://www.who.int/blindness/GLOBALDATAFINALforweb.pdf> (2012).

Goodman et al.(eds), Goodman And Gilman's: The Pharmacological Bases of Therapeutics, Pergamon Press (1990).

Great Britain Patent Application No. GB1700104.1, Search Report, dated Oct. 31, 2017.

International Application No. PCT/IB2018/050063, International Preliminary Report on Patentability, dated Jul. 9, 2019.

Madsen et al., A humanized model for multiple sclerosis using HLA-DR2 and a human T-cell receptor, Nature Genetics, 23(3):343-7 (Nov. 1999).

Strau et al, Negative and positive selection by HLA-DR3(DRw17) molecules in transgenic mice, Immunogenetics, 40(2):104-8 (1994).

Yamaki et al., The sequence of human retinal S-antigen reveals similarities with alpha-transduction, FEBS Letters, 234(1):39-43 (Jul. 1988).

* cited by examiner

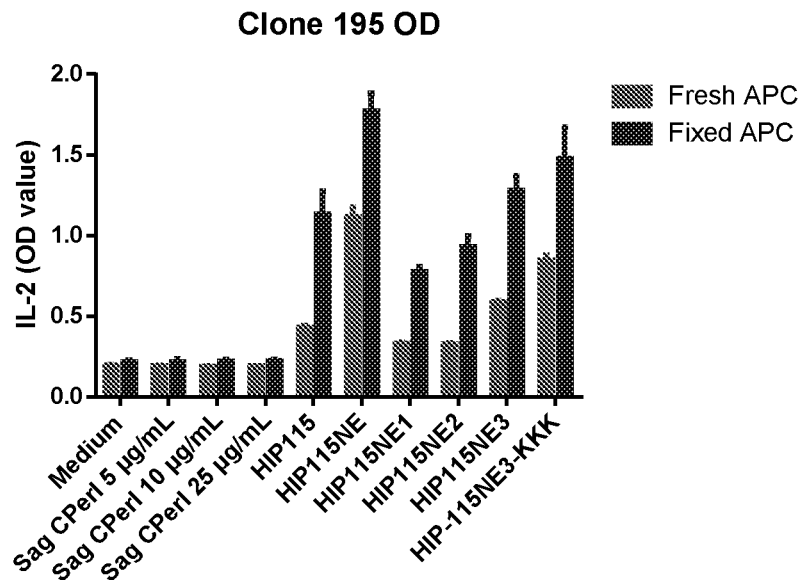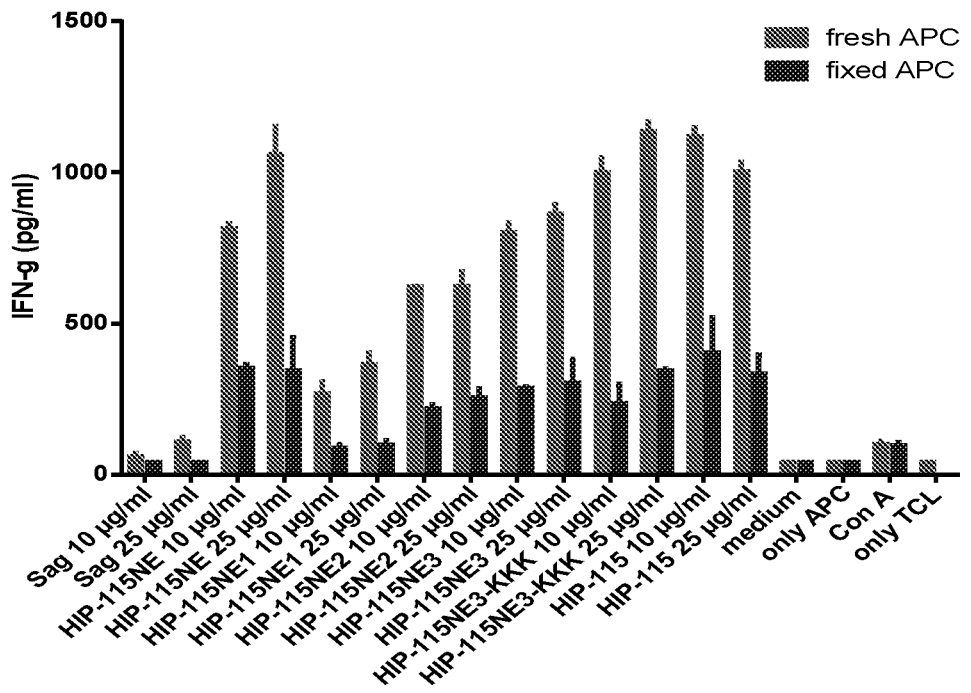
FIG. 2

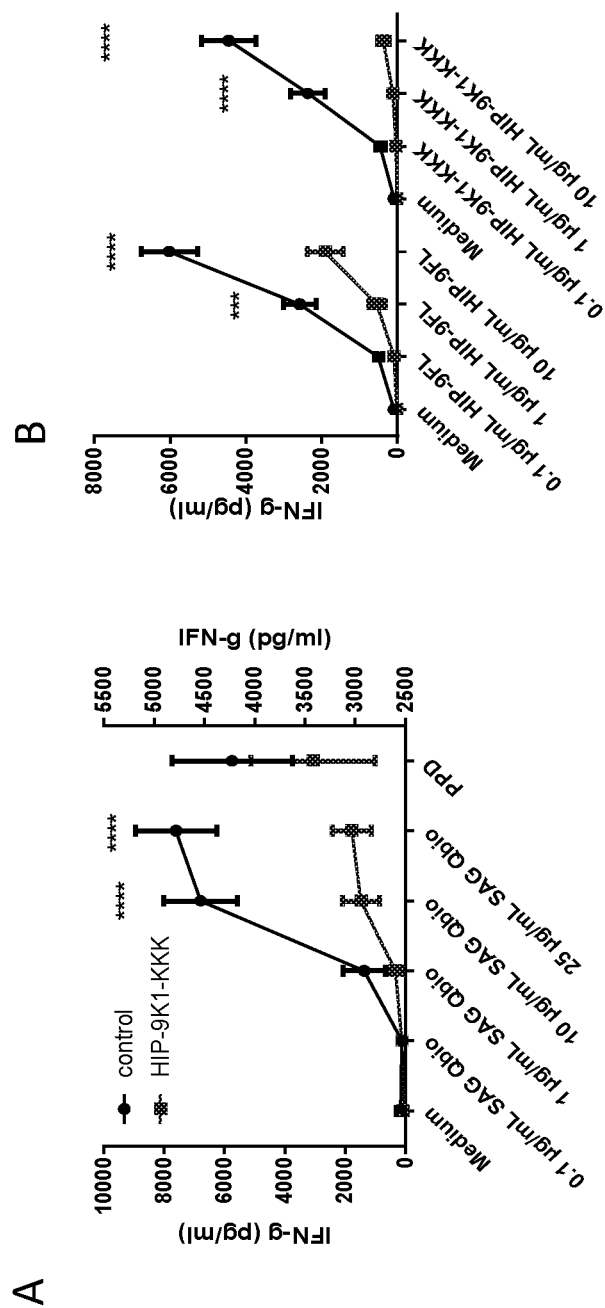
FIG. 11 (1/2)

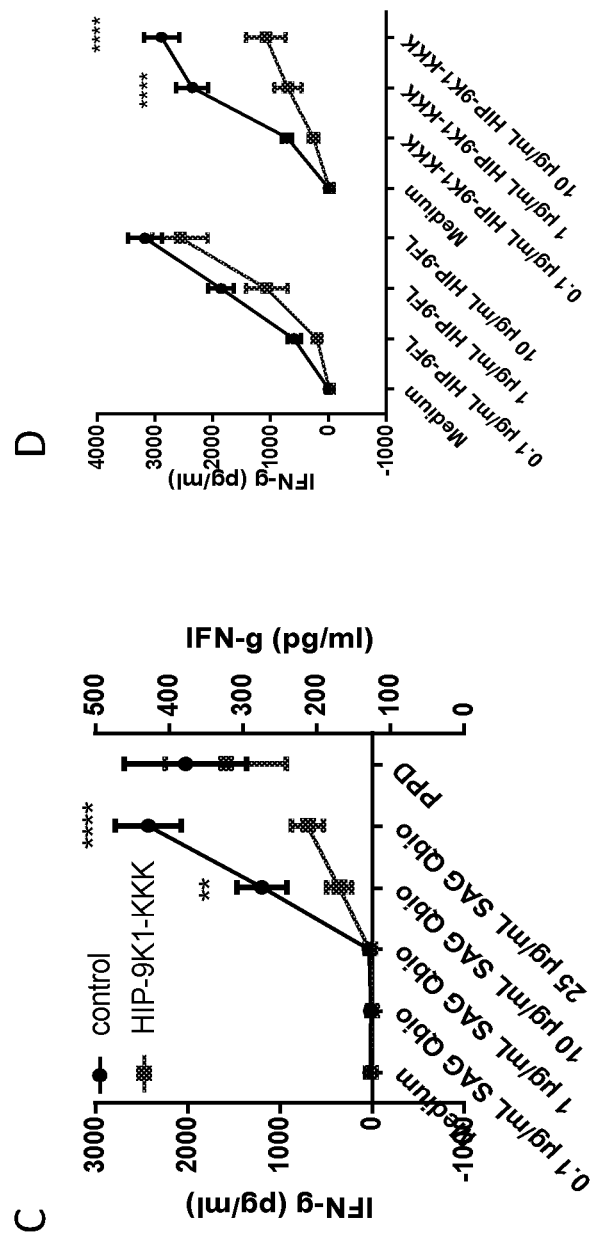
FIG. 11 (2/2)

US 11,542,316 B2

S-ARRESTIN PEPTIDES AND THERAPEUTIC USES THEREOF

CROSS-REFERENCE TO RELATED APPLICATIONS

This application is a U.S. National Phase of International Patent Application No. PCT/IB2018/050063, filed Jan. 4, 2018, which claims priority benefit of Application No. 1700104.1, filed on Jan. 4, 2017, in the United Kingdom.

INCORPORATION BY REFERENCE OF MATERIALS SUBMITTED ELECTRONICALLY

This application contains, as a separate part of the disclosure, a Sequence Listing in computer readable form (Filename: 54439_Seqlisting.txt; Size: 16,728 bytes; Created: Jun. 27, 2019), which is incorporated by reference in its entirety.

FIELD OF THE INVENTION

The present invention relates to a composition which comprises peptides derived from S-Arrestin (retinal arrestin, S-antigen, S-Ag). The composition or peptides may be useful in the prevention and/or suppression of S-Ag autoimmunity, which is useful in the treatment and/or prevention of uveitis.

BACKGROUND TO THE INVENTION

Uveitis describes a group of diseases associated with inflammation of the uvea. The uvea is a region of the eye located between the sclera and the retina, and includes the iris, ciliary body and choroid. The uvea provides most of the blood supply to the retina. The associated diseases are not restricted to those affecting the uvea directly, and adjacent structures such as the retina, optic nerve, lens, vitreous and sclera can be affected in manifestations of uveitis.

All forms of uveitis are characterised by an inflammatory cellular infiltrate, commonly visualised using a biomicroscope. In 2010, it was estimated that 285 million people were visually impaired; of these, 39 million were blind, and it was approximated that 10% of the cases were due to uveitis. (Global data on visual impairments, The World Health Report, WHO (2010) http COLON SLASH SLASH www.who.int/blindness/GLOBALDATAFINALforweb.pdf Present treatments for uveitis include the use of glucocorticoid steroids and other immunosuppressive agents such as methotrexate.

There is, however, a need in the art for alternative treatments for uveitis. The present invention addresses this need.

SUMMARY OF ASPECTS OF THE INVENTION

The present inventors have identified a number of peptides derived from S-Ag which may be useful in the prevention and/or treatment of uveitis.

Thus, in a first aspect, the present invention provides a peptide which comprises all or a portion of the following S-Ag derived peptides:
KKKVIFKKISRDKSVTIYLGKKK (SEQ ID No. 15)
RERRGIALDGKIKHE (SEQ ID No. 19)
LTKTLTLLPLLANNRERR (SEQ ID No. 25)
KKKAFVEQVANVVLKKK (SEQ ID No. 34)
KKKVIGLTFRRDLYFSRVQVYPPVGKKK (SEQ ID No. 36)
KKKGILVSYQIKVKKKK (SEQ ID No. 46)

In a preferred aspect the peptide is capable of binding to an MHC molecule in vitro and being presented to a T cell without antigen processing, In a second aspect the present invention provides a composition comprising a plurality of peptides, including one or more peptides according to the first aspect.

In a third aspect there is provided a peptide according to the first aspect or a composition according to the second aspect for use in suppressing or preventing the production of T cells specific for S-Ag and/or S-Ag autoantibodies in vivo.

In a fourth aspect there is provided a peptide according to the first aspect or a composition according to the second aspect for use in treating or preventing uveitis in a subject.

In a fifth aspect the present invention provides a method for suppressing or preventing the production of S-Ag autoantibodies in a subject, which comprises the step of administration of a peptide according to the first aspect, or a composition according to the second aspect, to the subject.

In a sixth aspect the present invention provides a method for treating or preventing uveitis in a subject, which comprises the step of administration of a peptide according to the first aspect, or a composition according to the second aspect, to the subject.

LIST OF FIGURES

FIG. 1: Immunogenicity of HIP-115 in DR3 mice. Mice were immunized with 50 µg HIP-115/CFA or PBS/CFA in the tail base. After 10 days, LN and spleens were harvested and cultured with 10 µg/ml and 25 µg/ml of HIP-115. Supernatants were collected after 72 h. Cell activation was measured by IFN-γ ELISA. (A) Immunogenicity in LN. (B) Immunogenicity in spleens. CFA, Complete Freund's Adjuvant; LN, lymph nodes.

FIG. 2: identification of apitopes within HIP-115. (A) DR3 mice were immunized with SAg and hybridomas were generated. 5×10⁴ SAg-specific hybridoma cells were cultured with 5×10⁴ fresh or fixed commercial APC (VAVY) cells. T cell proliferation was measured by IL-2 ELISA on supernatants collected after 48 h. The graph represents the mean of duplicate measurements±SEM. (B) DR3 mice were immunized with HIP-115 and a T cell line was established. Ten days after immunization the LN and spleens were harvested and cultured with different concentrations of peptide (0.1-1-2.5 and 5 µg/ml); 2×10⁶ cells/ml APC+1×10⁶ cells/ml CD4 T cells per well. At day 7 the cells were re-stimulated with the same concentrations of peptide. On day 14 an APIPS test was done using commercial APC (VAVY). After 24 h, antigen-induced T cell activation was measured by IFN-γ ELISA and shown as IFN-γ concentration (pg/ml). The graph represents the mean of duplicate measurements±SEM. LN, lymph nodes; APC, Antigen presenting cell; APIPS, Antigen Processing Independent Presentation System.

Figure 3:
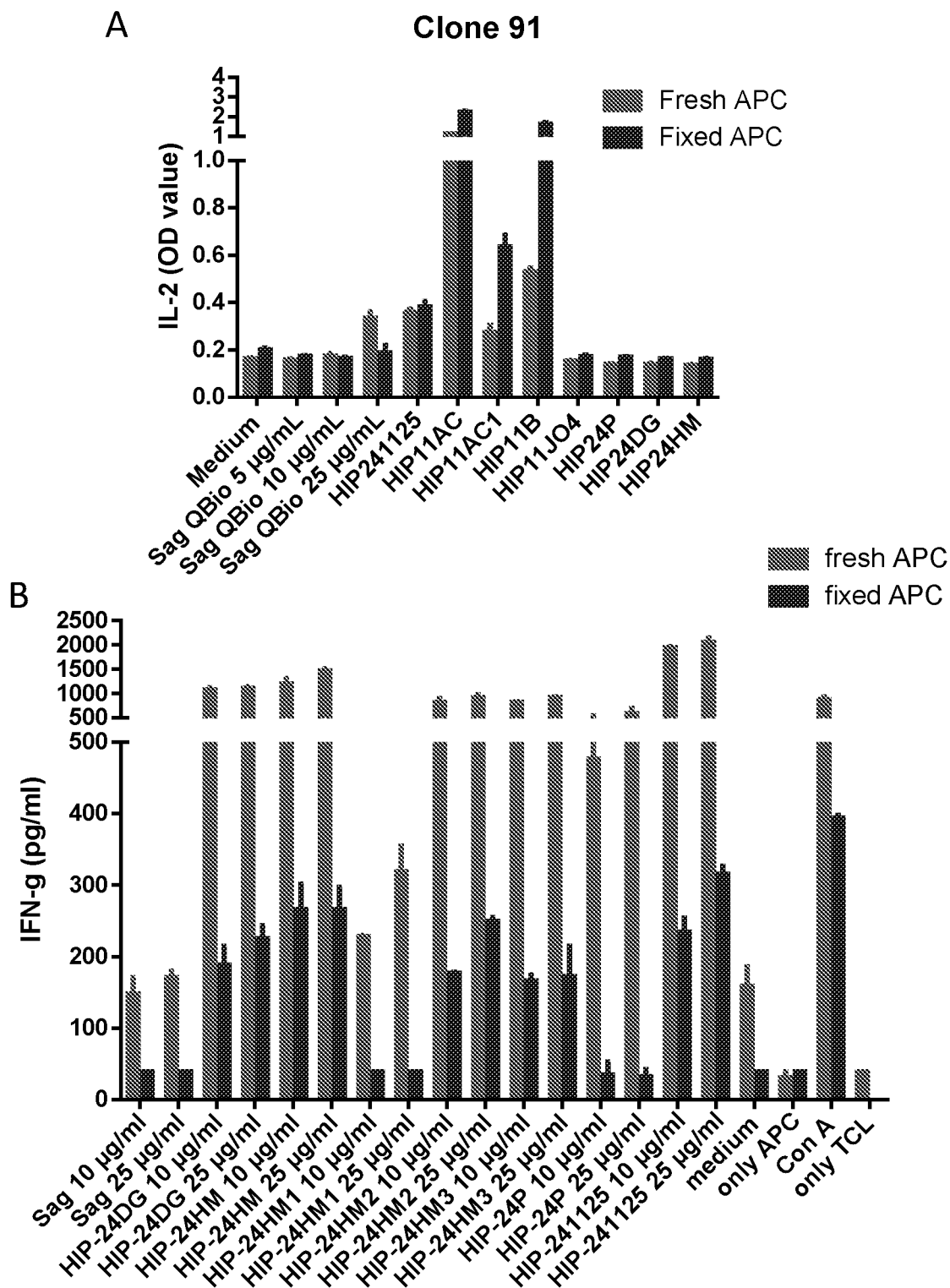

FIG. 3: identification of apitopes within HIP-241125. (A) DR3 mice were immunized with SAg and hybridomas were generated. 5×10⁴ SAg-specific hybridoma cells were cultured with 5×10⁴ fresh or fixed commercial APC (VAVY) cells. T cell proliferation was measured by IL-2 ELISA on supernatants collected after 48 h. The graph represents the mean of duplicate measurements±SEM. (B) DR3 mice were immunized with HIP-241125+HIP-24DG and a T cell line was established. Ten days after immunization the LN and spleens were harvested and cultured with different concentrations of peptide (0.1-1-2.5 and 5 µg/ml); $2 \times 10^6$ cells/ml APC+$1 \times 10^6$ cells/ml CD4 T cells per well. At day 7 the cells were re-stimulated with the same concentrations of peptide. On day 14 an APIPS test was done using commercial APC (VAVY). After 24 h, antigen-induced T cell activation was measured by IFN-γ ELISA and shown as IFN-γ concentration (pg/ml). The graph represents the mean of duplicate measurements±SEM. LN, lymph nodes; APC, Antigen presenting cell; APIPS, Antigen Processing Independent Presentation System.

Figure 4:
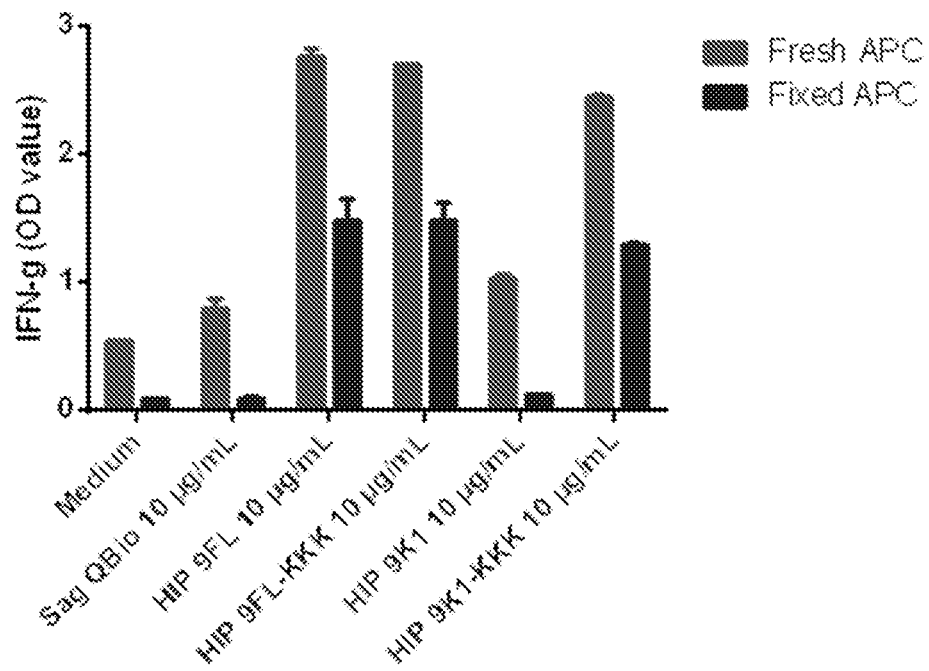

FIG. 4: Identification of apitopes within HIP-9FL. DR2 mice were immunized with HIP-9FL-KKK and a T cell line was established. Ten days after immunization the LN and spleens were harvested and cultured with different concentrations of peptide (0.1-1-2.5 and 5 µg/ml); $2 \times 10^6$ cells/ml APCs+$1 \times 10^6$ cells/ml CD4 T cells per well. At day 7 the cells were re-stimulated with the same concentrations of peptide. On day 21 an APIPS test was done using commercial APC (MGAR). After 24 h, antigen-induced T cell activation was measured by IFN-γ ELISA and shown as OD values. The graph represents the mean of duplicate measurements±SEM. LN, lymph nodes; APC, Antigen presenting cell; APIPS, Antigen Processing Independent Presentation System.

Figure 5:
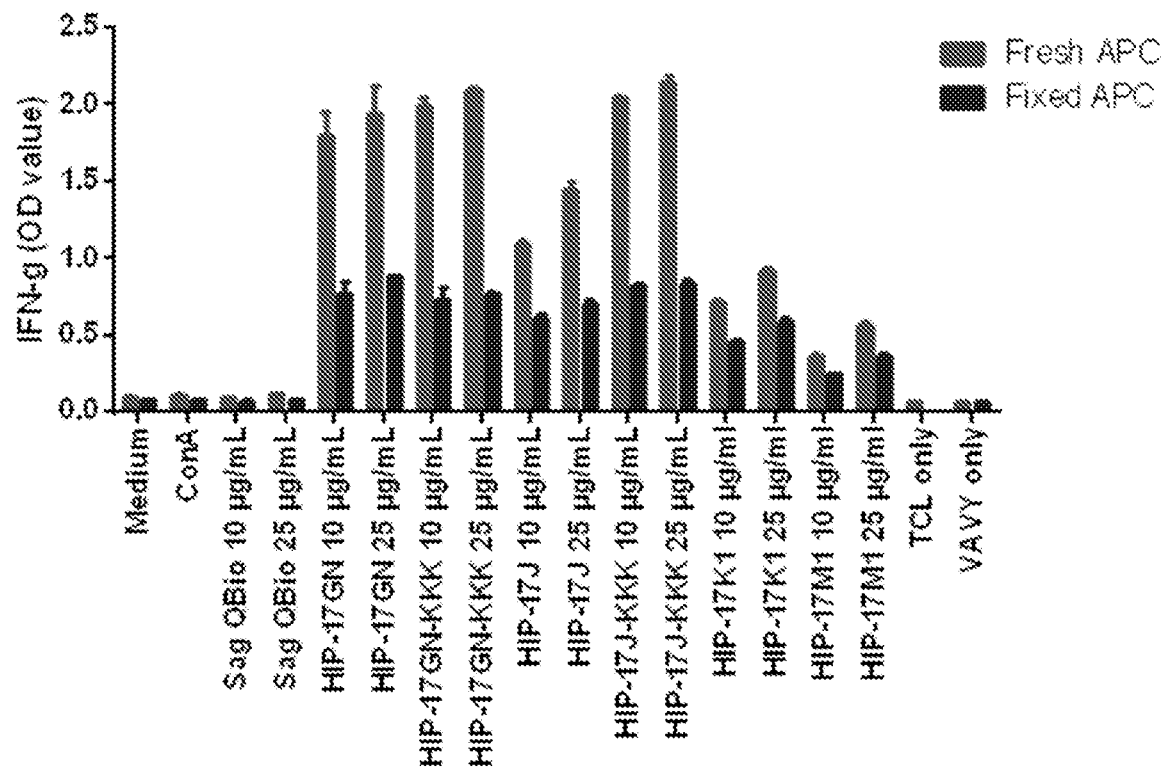

FIG. 5: Identification of apitopes within HIP-17GN. DR3 mice were immunized with HIP-17GN and a T cell line was established. Ten days after immunization the LN and spleens were harvested and cultured with different concentrations of peptide (0.1-1-2.5 and 5 µg/ml); $2 \times 10^6$ cells/ml APC+$1 \times 10^6$ cells/ml CD4 T cells per well. At day 7 the cells were re-stimulated with the same concentrations of peptide. On day 14 an APIPS test was done using commercial APC (VAVY). After 24 h, antigen-induced T cell activation was measured by IFN-γ ELISA and shown as OD values. The graph represents the mean of triplicate measurements±SEM. LN, lymph nodes; APC, Antigen presenting cell; APIPS, Antigen Processing Independent Presentation System.

Figure 6:
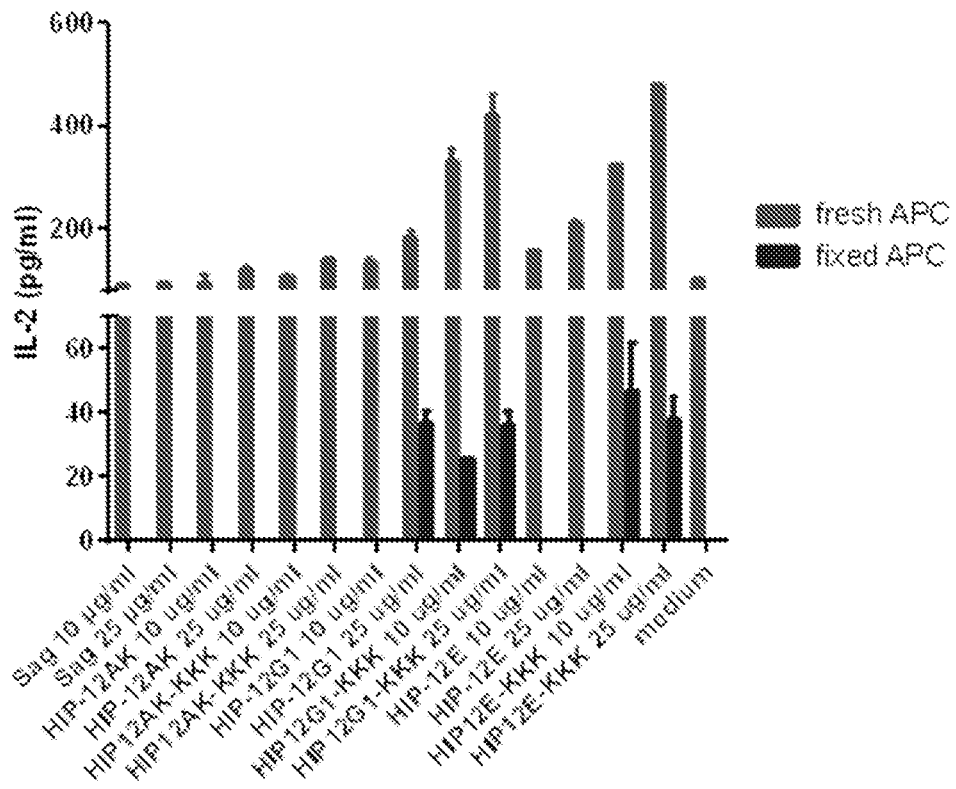

FIG. 6: Identification of apitopes within HIP-12AK. DR3 mice were immunized with HIP-12AK and a T cell line was established. Ten days after immunization the LN and spleens were harvested and cultured with different concentrations of peptide (0.1-1-2.5 and 5 µg/ml); $2 \times 10^6$ cells/ml APC+$1 \times 10^6$ cells/ml CD4 T cells per well. At day 7 the cells were re-stimulated with the same concentrations of peptide. On day 14 an APIPS test was done using commercial APC (VAVY). After 24 h, antigen-induced T cell activation was measured by IFN-γ ELISA and shown as IFN-γ concentration (pg/ml). The graph represents the mean of duplicate measurements±SEM. LN, lymph nodes; APC, Antigen presenting cell; APIPS, Antigen Processing Independent Presentation System.

Figure 7:
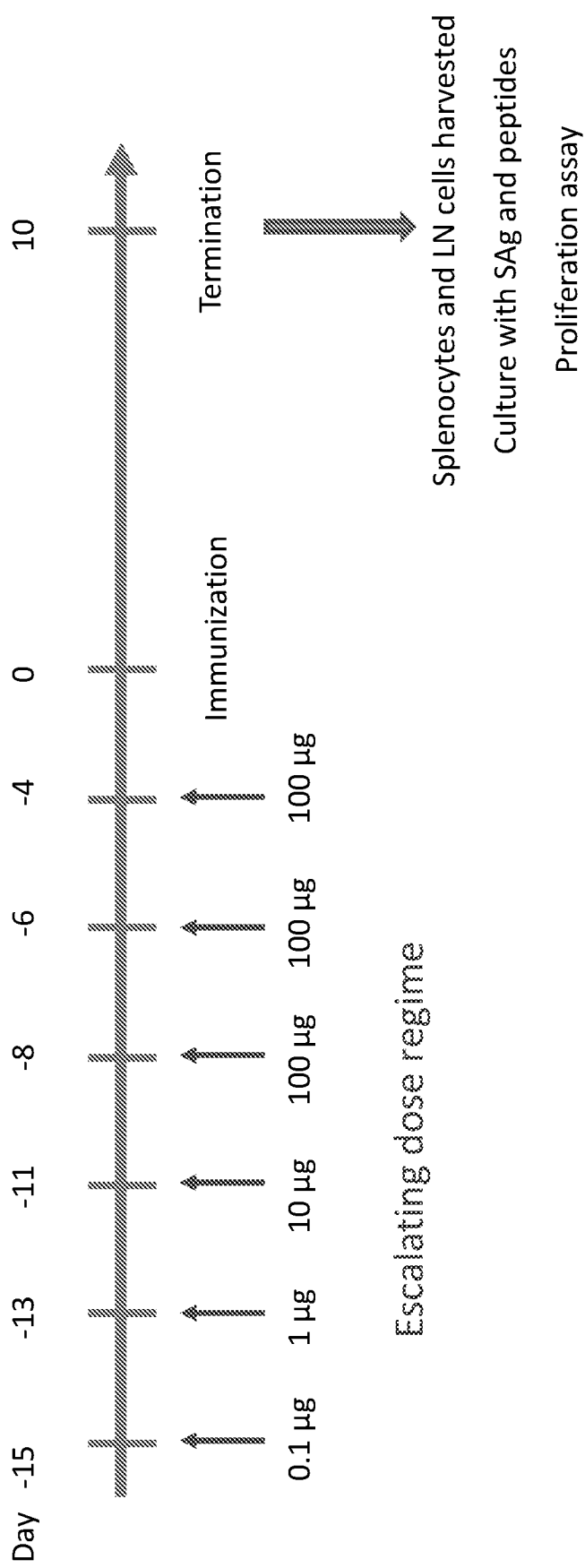

FIG. 7: Ex vivo tolerisation protocol. Mice are injected subcutaneously in the flank with 0.1 µg/ml, 1 µg/ml and 10 µg/ml peptide on days −15, −13 and −11, followed by 3 injections of 100 µg/ml on days −8, −6 and −4 (escalating dose regime). On day 0, mice are immunized subcutaneously at the base of the tail with SAg/CFA or peptide/CFA. Mice are sacrificed 10 days after immunization to measure proliferation of LN cells and splenocytes upon SAg or peptide restimulation. LN, lymph nodes.

Figure 8:
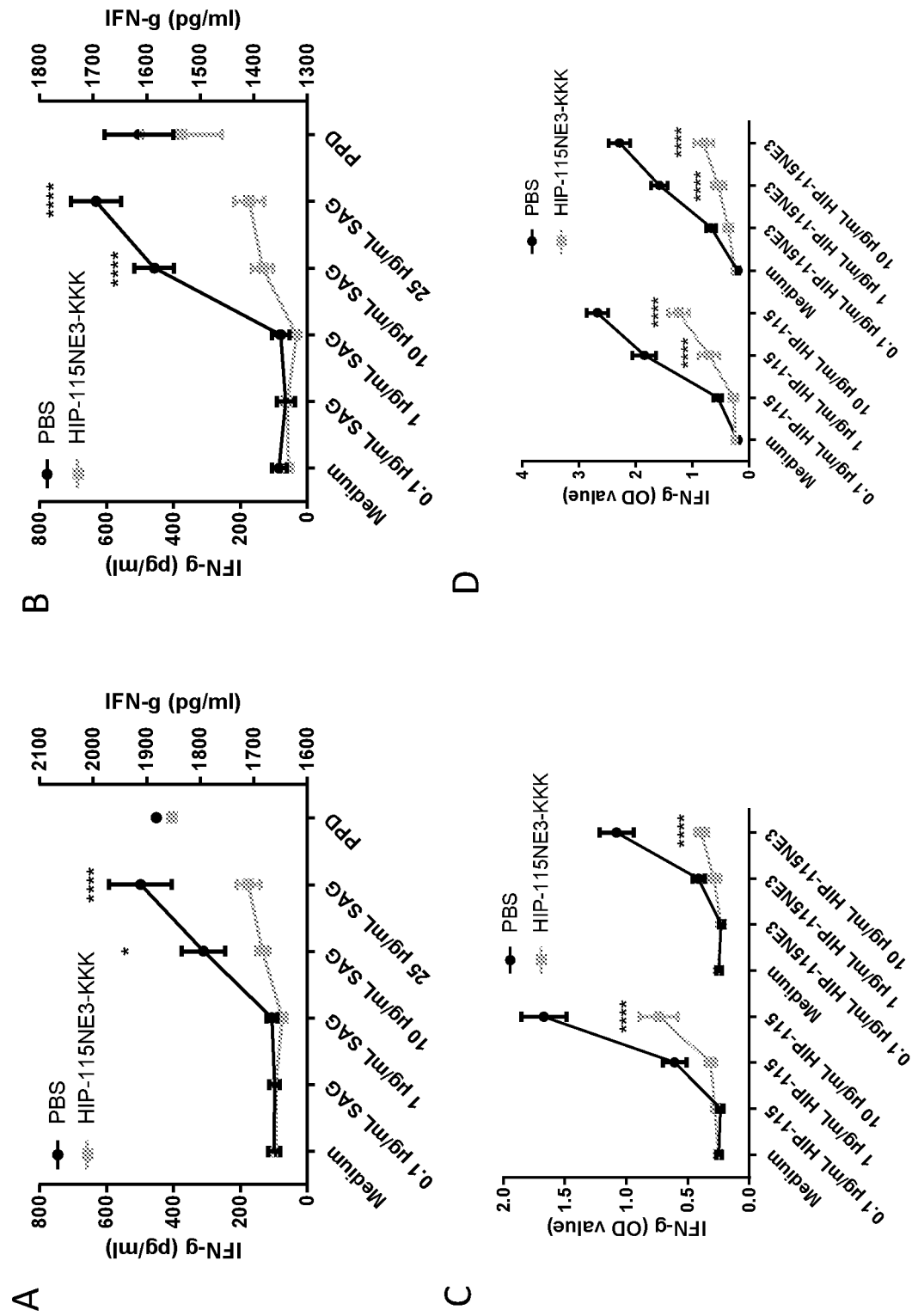

FIG. 8: Ex vivo tolerance induction by HIP-115NE3-KKK apitope. DR3 mice are injected subcutaneously in the flank with 0.1 µg/ml, 1 µg/ml and 10 µg/ml HIP-115NE3-KKK on days −15, −13 and −11, followed by 3 injections of 100 µg/ml on days −8, −6 and −4 (escalating dose regime). On day 0, mice are immunized subcutaneously at the base of the tail with HIP-115/CFA. Mice are sacrificed 10 days after immunization to measure proliferation of LN cells and splenocytes upon SAg or peptide restimulation. Data represent mean±SEM of the concentration or OD values for the PBS-treated mice (black lines) and peptide-treated mice (color lines). Two-way ANOVA was used to measure overall treatment effects on T cell activation and p-values are written in the graphs. Bonferonni post-hoc testing was used and significant differences are indicated in the graphs (* $p<0.05$; **** $p<0.0001$). LN, lymph nodes. (A) Tolerisation against SAg in LN. IFN-γ production expressed as IFN-γ concentration (pg/ml). (B) Tolerisation against SAg in spleen. IFN-γ production expressed as IFN-γ concentration (pg/ml). (C) Tolerisation against HIP-115 and HIP-115NE3 peptides in LN. IFN-γ production expressed as OD values. (D) Tolerisation against HIP-115 and HIP-115NE3 peptides in spleen. IFN-γ production expressed as OD values.

Figure 9:
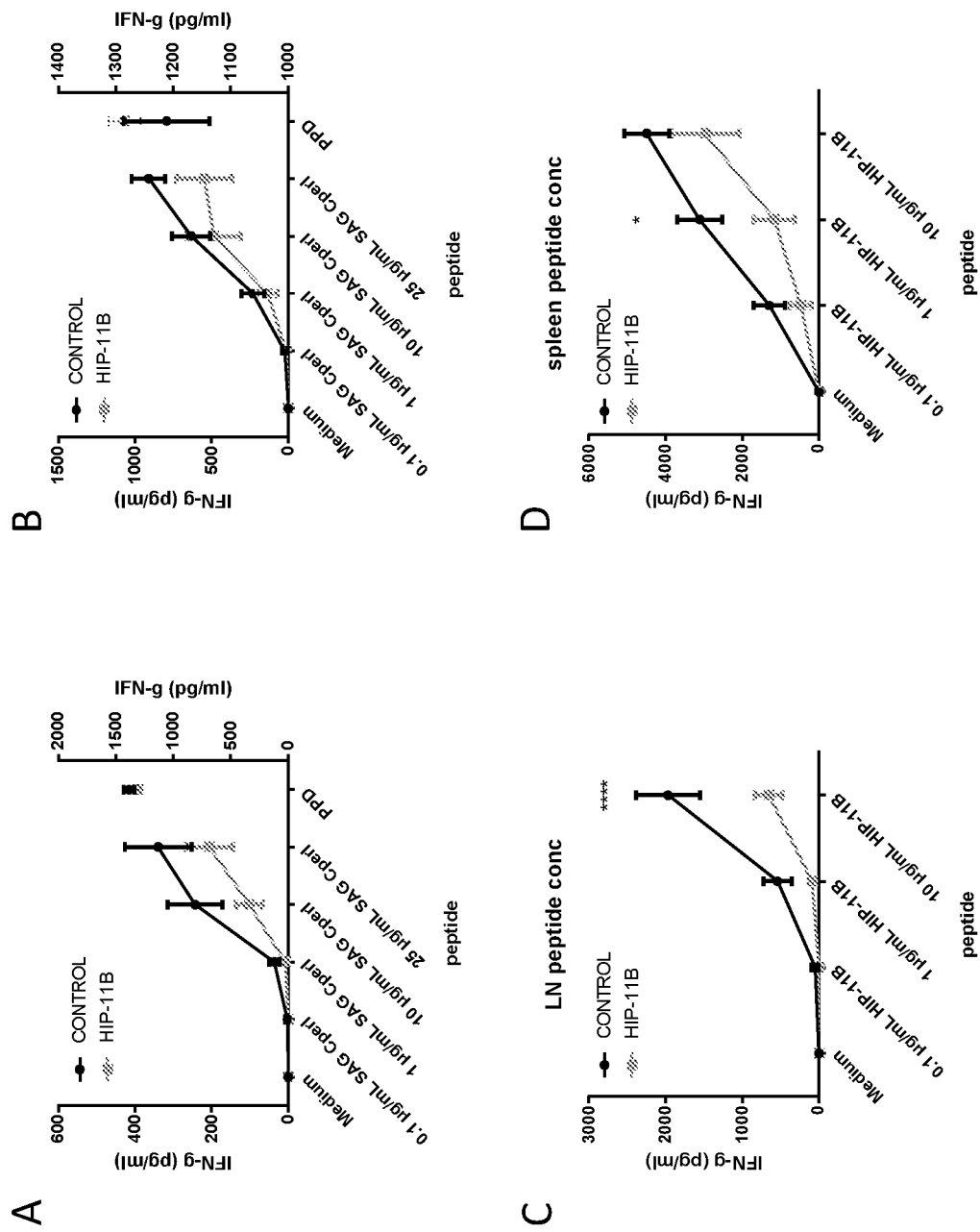

FIG. 9: Ex vivo tolerance induction by HIP-11B apitope. DR3 mice are injected subcutaneously in the flank with 0.1 µg/ml, 1 µg/ml and 10 µg/ml HIP-11B on days −15, −13 and −11, followed by 3 injections of 100 µg/ml on days −8, −6 and −4 (escalating dose regime). On day 0, mice are immunized subcutaneously at the base of the tail with HIP-11B/CFA. Mice are sacrificed 10 days after immunization to measure proliferation of LN cells and splenocytes upon SAg or peptide restimulation. Data represent mean±SEM of the concentration values for the PBS-treated mice (black lines) and peptide-treated mice (color lines). IFN-γ production expressed as IFN-γ concentration (pg/ml). Two-way ANOVA was used to measure overall treatment effects on T cell activation and p-values are written in the graphs. Bonferonni post-hoc testing was used and significant differences are indicated in the graphs (* $p<0.05$; **** $p<0.0001$). LN, lymph nodes. (A) Tolerisation against SAg in LN. (B) Tolerisation against SAg in spleen. (C) Tolerisation against HIP-11B peptide in LN. (D) Tolerisation against HIP-11B peptide in spleen.

Figure 10:
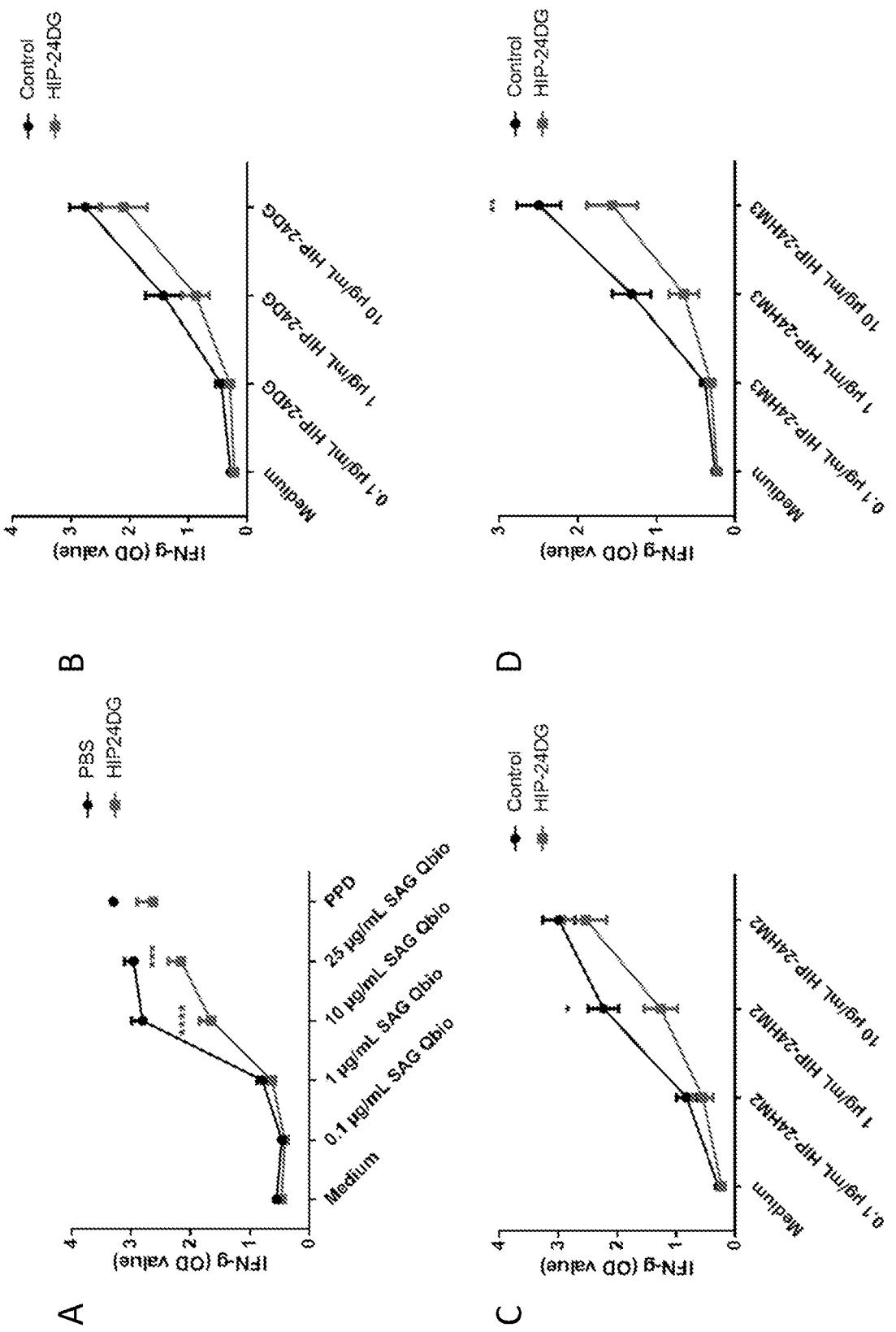

FIG. 10: Ex vivo tolerance induction by HIP-24DG apitope. DR3 mice are injected subcutaneously in the flank with 0.1 µg/ml, 1 µg/ml and 10 µg/ml HIP-24DG on days −15, −13 and −11, followed by 3 injections of 100 µg/ml on days −8, −6 and −4 (escalating dose regime). On day 0, mice are immunized subcutaneously at the base of the tail with HIP-24DG+HIP-24HM/CFA. Mice are sacrificed 10 days after immunization to measure proliferation of LN cells and splenocytes upon SAg or peptide restimulation. Data represent mean±SEM of the OD values for the PBS-treated mice (black lines) and peptide-treated mice (color lines). IFN-γ production expressed as OD values. LN, lymph nodes. Two-way ANOVA was used to measure overall treatment effects on T cell activation and p-values are written in the graphs. Bonferonni post-hoc testing was used and significant differences are indicated in the graphs (* $p<0.05$;  $p<0.01$; * $p<0.001$; **** $p<0.0001$). LN, lymph nodes. (A) Tolerisation against SAg in LN. (B) Tolerisation against HIP-24DG in LN. (C) Tolerisation against HIP-24HM2 peptide in LN. (D) Tolerisation against HIP-24HM3 peptide in LN.

FIG. 11: Ex vivo tolerance induction by HIP-9K1-KKK apitope. DR2 mice are injected subcutaneously in the flank with 0.1 µg/ml, 1 µg/ml and 10 µg/ml HIP-9K1-KKK on days −15, −13 and −11, followed by 3 injections of 100 µg/ml on days −8, −6 and −4 (escalating dose regime). On day 0, mice are immunized subcutaneously at the base of the tail with HIP-9FL/CFA. Mice are sacrificed 10 days after immunization to measure proliferation of LN cells and splenocytes upon SAg or peptide restimulation. Data represent mean±SEM of the concentration values for the PBS-treated mice (black lines) and peptide-treated mice (color lines). IFN-γ production expressed as IFN-γ concentration (pg/ml). Two-way ANOVA was used to measure overall treatment effects on T cell activation and p-values are written in the graphs. Bonferonni post-hoc testing was used and significant differences are indicated in the graphs (* $p<0.05$; **** $p<0.0001$). LN, lymph nodes. (A) Tolerisation against SAg in LN. (B) Tolerisation against HIP-9FL and HIP-9K1-KKK in LN. (C) Tolerisation against SAg in spleen. (D) Tolerisation against HIP-9FL and HIP-9K1-KKK in spleen.

Figure 12:
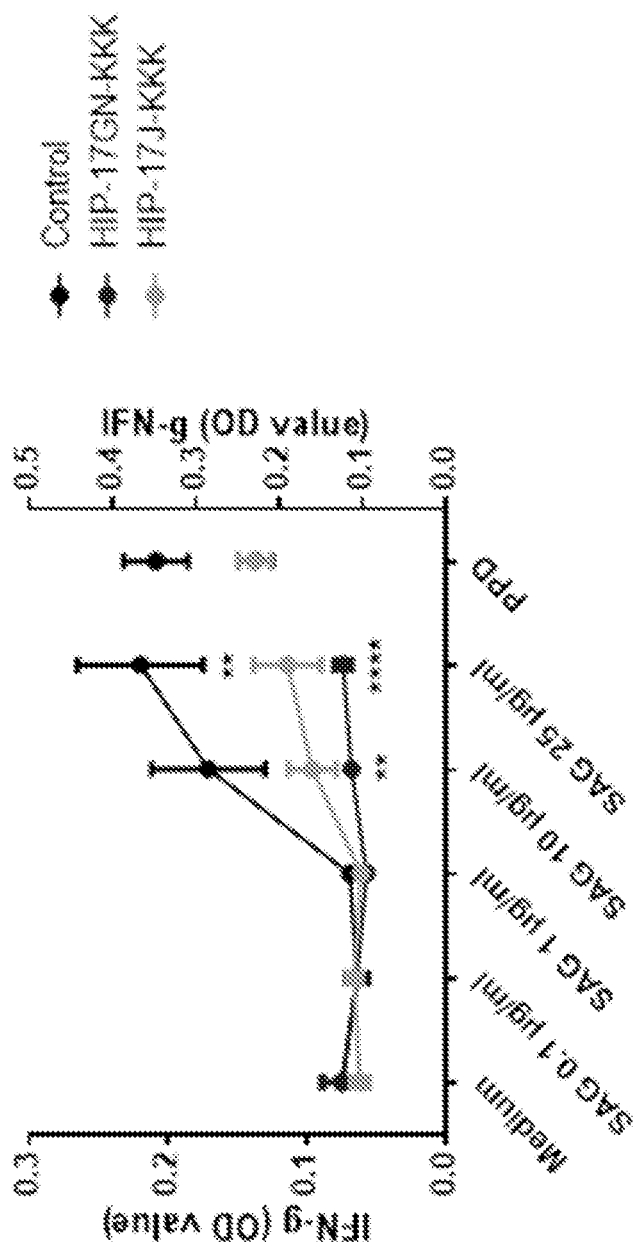

FIG. 12: Ex vivo tolerance induction by HIP-17GN-KKK and HIP-17J-KKK apitopes. DR3 mice are injected subcutaneously in the flank with 0.1 μg/ml, 1 μg/ml and 10 μg/ml HIP-17GN-KKK or HIP-17J-KKK on days −15, −13 and −11, followed by 3 injections of 100 μg/ml on days −8, −6 and −4 (escalating dose regime). On day 0, mice are immunized subcutaneously at the base of the tail with HIP-17GN/CFA. Mice are sacrificed 10 days after immunization to measure proliferation of LN cells and splenocytes upon SAg or peptide restimulation. Data represent mean±SEM of the OD values for the PBS-treated mice (black lines) and peptide-treated mice (color lines). Tolerisation against SAg in spleen. IFN-γ production expressed as OD values. Two-way ANOVA was used to measure overall treatment effects on T cell activation and p-values are written in the graphs. Bonferonni post-hoc testing was used and significant differences are indicated in the graphs ( $p<0.01$; ** $p<0.0001$).

Figure 13:
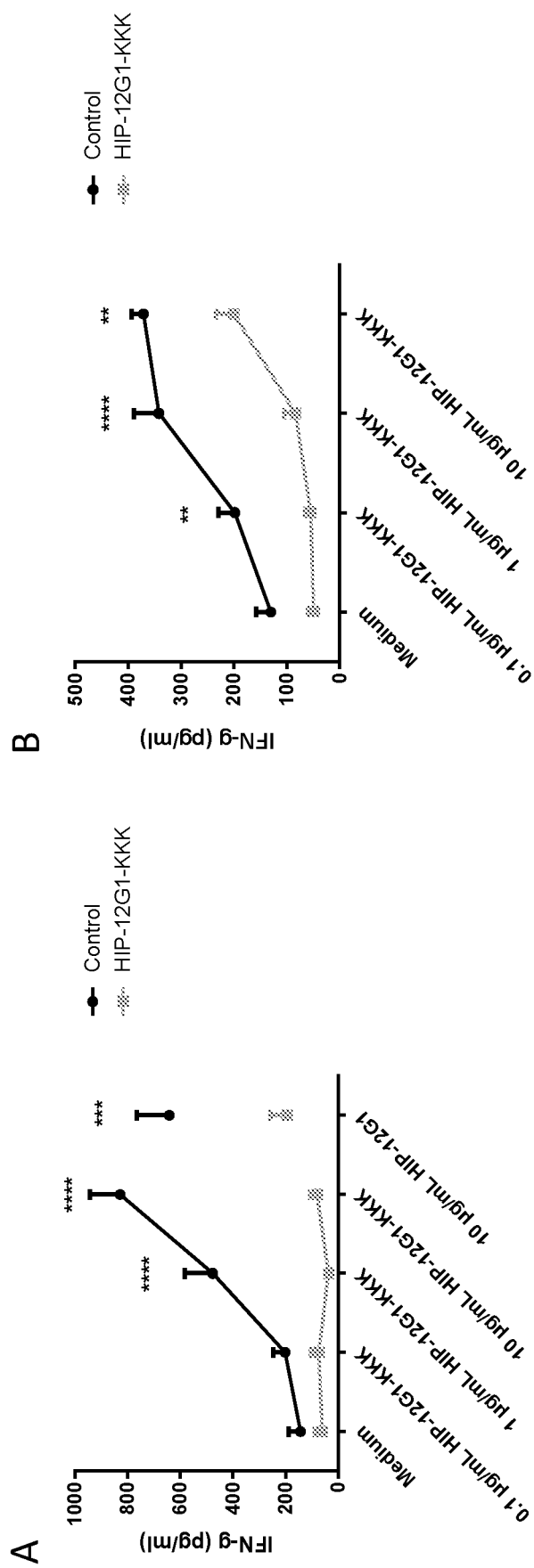

FIG. 13: Ex vivo tolerance induction by HIP-12G1-KKK apitope. DR2 mice are injected subcutaneously in the flank with 0.1 μg/ml, 1 μg/ml and 10 μg/ml HIP-12G1-KKK on days −15, −13 and −11, followed by 3 injections of 100 μg/ml on days −8, −6 and −4 (escalating dose regime). On day 0, mice are immunized subcutaneously at the base of the tail with HIP-12AK/CFA. Mice are sacrificed 10 days after immunization to measure proliferation of LN cells and splenocytes upon SAg or peptide restimulation. Data represent mean±SEM of the concentration values for the PBS-treated mice (black lines) and peptide-treated mice (color lines). IFN-γ production expressed as IFN-γ concentration (pg/ml). Two-way ANOVA was used to measure overall treatment effects on T cell activation and p-values are written in the graphs. Bonferonni post-hoc testing was used and significant differences are indicated in the graphs ( $p<0.01$; * $p<0.001$: **** $p<0.0001$). LN, lymph nodes. (A) Tolerisation against HIP-12G1-KKK and HIP-12G1 in LN. (B) Tolerisation against HIP-12G1-KKK in spleen.

Figure 14:
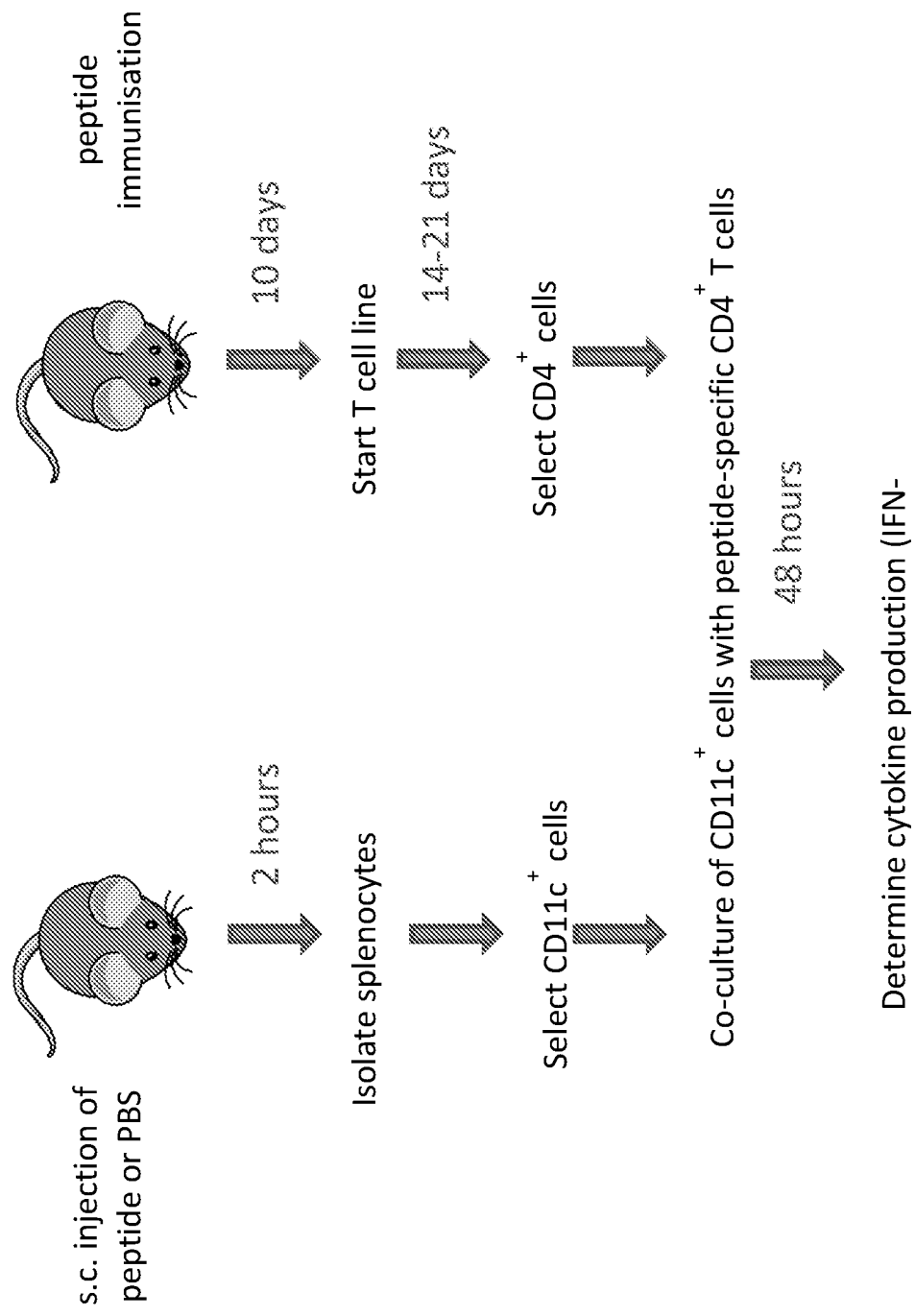

FIG. 14: In vivo presentation protocol. Mice are immunized with peptide/CFA and a T cell line is established. For this, ten days after immunization the LN and spleens are harvested and cultured with different concentrations of peptide; $2\times10^6$ cells/ml APC+$1\times10^6$ cells/ml CD4$^+$ cells per well. At day 7 the cells are re-stimulated with fresh APC and the same concentrations of peptide. After 14 to 21 days, CD4$^+$ cells are isolated from these cultures by magnetic bead isolation. These CD4$^+$ cells are co-cultured with CD11c$^+$ (dendritic) cells isolated by magnetic bead isolation from spleens of mice s.c. injected with peptide 2 hours before. Control mice receive a s.c. injection of PBS. After 48 hours, supernatant is collected and cytokine response (IFN-γ) is measured. LN, lymph nodes; APC, Antigen presenting cell; s.c. subcutaneous.

Figure 15:
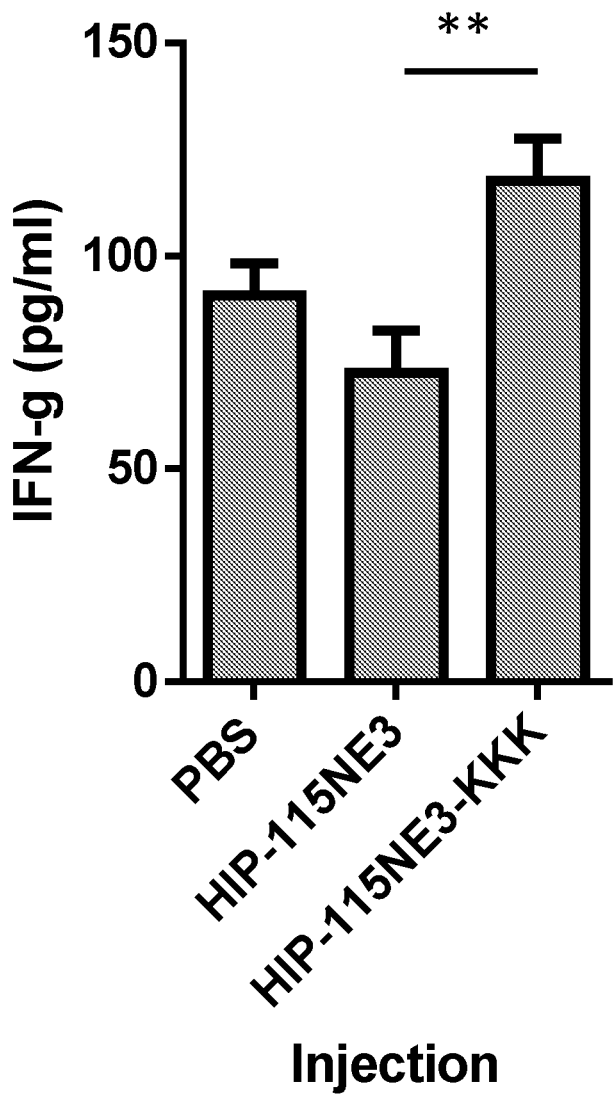

FIG. 15: In vivo presentation of HIP-115 nested peptides in DR3 mice. DR3 mice were immunized with HIP-115/CFA and a T cell line was established. For this, ten days after immunization the LN and spleens were harvested and cultured with different concentrations of peptide (0.1-1-2.5 and 5 μg/ml); $2\times10^6$ cells/ml APC+$1\times10^6$ cells/ml CD4$^+$ cells per well. At day 7 the cells were re-stimulated with fresh APC and the same concentrations of peptide. After 14 days, CD4$^+$ cells were isolated from these cultures by magnetic bead isolation. These CD4$^+$ cells were co-cultured with CD11c (dendritic) cells isolated by magnetic bead isolation from spleens of DR3 mice s.c. injected with peptides HIP-115NE3, HIP-115NE3-KKK or PBS 2 hours before. After 48 hours, supernatant was collected and IFN-γ production was measured by ELISA. Data are presented as the mean IFN-γ concentration±SEM (One-way ANOVA with Dunn's multiple comparison, * $p<0.05$, ** $p<0.01$). LN, lymph nodes; APC, Antigen presenting cell; s.c. subcutaneous.

Figure 16:
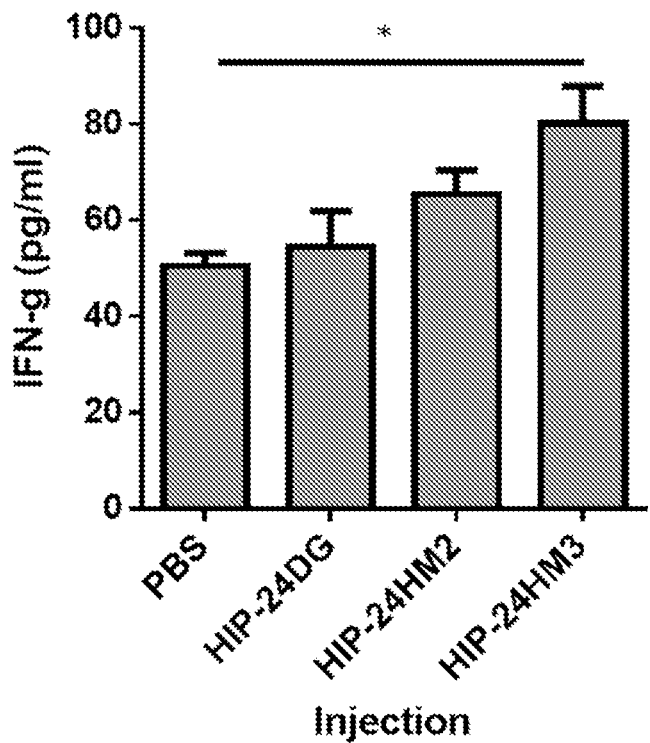

FIG. 16: In vivo presentation of HIP-24 nested peptides in DR3 mice. DR3 mice were immunized with HIP-241125+HIP-24DG/CFA and a T cell line was established. For this, ten days after immunization the LN and spleens were harvested and cultured with different concentrations of peptide (0.3-1.2-3 and 6 μg/ml); $2\times10^6$ cells/ml APC+$1\times10^6$ cells/ml CD4$^+$ cells per well. At day 7 the cells were re-stimulated with fresh APC and the same concentrations of peptide. After 14 days, CD4$^+$ cells were isolated from these cultures by magnetic bead isolation. These CD4$^+$ cells were co-cultured with CD11c$^+$ (dendritic) cells isolated by magnetic bead isolation from spleens of DR3 mice s.c. injected with peptides HIP-24DG, HIP-24HM2, HIP-24HM3 or PBS 2 hours before. After 48 hours, supernatant was collected and IFN-γ production was measured by ELISA. Data are presented as the mean IFN-γ concentration±SEM (One-way ANOVA with Dunn's multiple comparison, * $p<0.05$). LN, lymph nodes; APC, Antigen presenting cell; s.c. subcutaneous.

Figure 17:
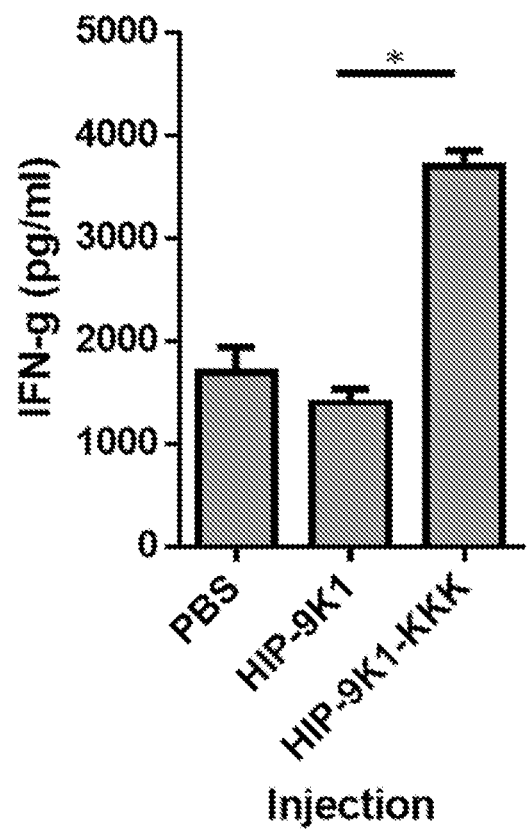

FIG. 17: In vivo presentation of HIP-9FL nested peptides in DR2 mice. DR2 mice were immunized with HIP-9FL-KKK/CFA and a T cell line was established. For this, ten days after immunization the LN and spleens were harvested and cultured with different concentrations of peptide (0.1-1-2.5 and 5 μg/ml); $2\times10^6$ cells/ml APC+$1\times10^6$ cells/ml CD4$^+$ cells per well. At day 7 and day 14, the cells were re-stimulated with fresh APC and the same concentrations of peptide. After 21 days, CD4$^+$ cells were isolated from these cultures by magnetic bead isolation. These CD4$^+$ cells were co-cultured with CD11c$^+$ (dendritic) cells isolated by magnetic bead isolation from spleens of DR2 mice s.c. injected with peptides HIP-9K1, HIP-9K1-KKK or PBS 2 hours before. After 48 hours, supernatant was collected and IFN-γ production was measured by ELISA. Data are presented as the mean IFN-γ concentration±SEM (One-way ANOVA with Dunn's multiple comparison, * $p<0.05$). LN, lymph nodes; APC, Antigen presenting cell; s.c. subcutaneous.

Figure 18:
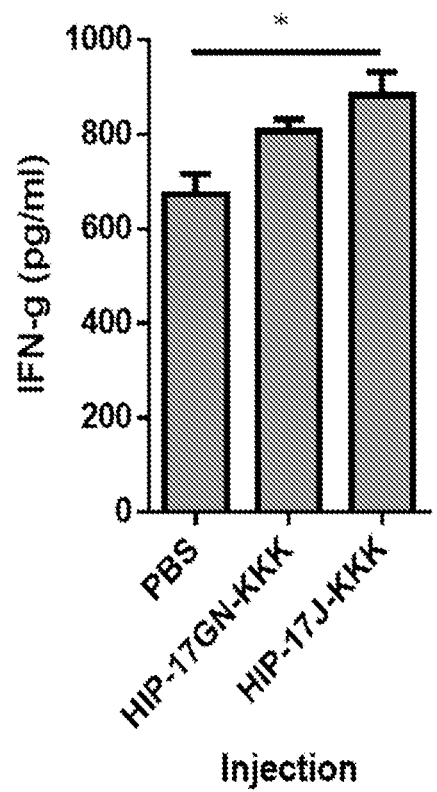

FIG. 18: In vivo presentation of HIP-17GN nested peptides in DR3 mice. DR3 mice were immunized with HIP-17GN/CFA and a T cell line was established. For this, ten days after immunization the LN and spleens were harvested and cultured with different concentrations of peptide (0.1-1-2.5 and 5 μg/ml); $2\times10^6$ cells/ml APC+$1\times10^6$ cells/ml CD4$^+$ cells per well. At day 7 the cells were re-stimulated with fresh APC and the same concentrations of peptide. After 14 days, CD4$^+$ cells were isolated from these cultures by magnetic bead isolation. These CD4$^+$ cells were co-cultured with CD11c$^+$ (dendritic) cells isolated by magnetic bead isolation from spleens of DR3 mice s.c. injected with peptides HIP-17GN-KKK, HIP-17J-KKK or PBS 2 hours before. After 48 hours, supernatant was collected and IFN-γ production was measured by ELISA. Data are presented as the mean IFN-γ concentration±SEM (One-way ANOVA with Dunn's multiple comparison, * p<0.05). LN, lymph nodes; APC, Antigen presenting cell; s.c. subcutaneous.

DETAILED DESCRIPTION

Peptides

The term "peptide" is used in the normal sense to mean a series of residues, typically L-amino acids, connected one to the other, typically by peptide bonds between the α-amino and carboxyl groups of adjacent amino acids. The term includes modified peptides and synthetic peptide analogues.

The peptide of the present invention may be made using chemical methods (Peptide Chemistry, A practical Textbook. Mikos Bodansky, Springer-Verlag, Berlin). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from the S-antigen protein, which may be followed by modification of one or both ends. The composition of a peptide may be confirmed by amino acid analysis or sequencing (e.g., the Edman degradation procedure).

For practical purposes, there are various other characteristics which the peptide may show. For example, it is important that the peptide is sufficiently stable in vivo to be therapeutically useful. The half-life of the peptide in vivo may be at least 10 minutes, 30 minutes, 4 hours, or 24 hours.

The peptide may also demonstrate good bioavailability in vivo. The peptide may maintain a conformation in vivo which enables it to bind to an MHC molecule at the cell surface without due hindrance.

The peptides used in the compositions and kits of the present invention may be all or a portion of the following S-Ag derived peptides:

IFKKISRDKSVTIYL (SEQ ID No 1)

KGKKVYVTLTCAFRY (SEQ ID No 2)

VIGLTFRRDLYFSRVQVYPPVG (SEQ ID No 3)

ESLLKKLGSNTYPFLLTFPDYLPCSVMLQPAPQDSGK (SEQ ID No 4)

SSVRLLIRKVQHAPLEM (SEQ ID No 5)

AEAAWQFFMSDKPLHLAVSLNKEIYF (SEQ ID No 6)

LTKTLTLLPLLANNRERRGIALDGKIKHEDTNLASSTIIKE (SEQ ID No 7)

IDRTVLGILVSYQIKVKLTVS (SEQ ID No 8)

NTEKTVKKIKAFVEQVANVVLYSSDYYVK (SEQ ID No 9)

In one aspect the peptides used in the compositions and kits of the present invention may be all or a portion of peptides shown in the Table below:

| Family | | Sequence | Seq. ID No. |
|---|---|---|---|
| HIP-115 | HIP-115 | MAASGKTSKSEPNHVIFKKISRDKSVTIYLGNRDYIDHVSQV | 10 |
| | HIP-115NE | HVIFKKISRDKSVTIYLGN | 11 |
| | HIP-115NE1 | KKISRDKSVTI | 12 |
| | HIP-115NE2 | FKKISRDKSVTIY | 13 |
| | HIP-115NE3 | VIFKKISRDKSVTIYLG | 14 |
| | HIP-115NE3-KKK | KKKVIFKKISRDKSVTIYLGKKK | 15 |
| HIP-241125 | HIP-241125 | LTLLPLLANNRERRGIALDGKIKHEDTNLASSTIIKEG | 16 |
| | HIP-11AC | NRERRGIALDGKIKHED | 17 |
| | HIP-11AC1 | ERRGIALDGKIKH | 18 |
| | HIP-11B | RERRGIALDGKIKHE | 19 |
| | HIP-11JO | DGKIKHEDTNLASSTIIKEG | 20 |
| | HIP-11JO1 | HEDTNLASST | 21 |
| | HIP-11JO2 | KHEDTNLASSTI | 22 |
| | HIP-11JO3 | IKHEDTNLASSTII | 23 |
| | HIP-11JO4 | KIKHEDTNLASSTIIK | 24 |
| | HIP-24DG | LTKTLTLLPLLANNRERR | 25 |
| | HIP-24HM | LTLLPLLANNRERRGIALDG | 26 |
| | HIP-24HM1 | LLANNRERRG | 27 |
| | HIP-24HM2 | PLLANNRERRGI | 28 |
| | HIP-24HM3 | LPLLANNRERRGIA | 29 |
| | HIP-24P | NNRERRGIALDGKIK | 30 |

-continued

| Family | | Sequence | Seq. ID No. |
|---|---|---|---|
| HIP-9F1 | HIP-9FL | VKKIKAFVEQVANVVLYSSDY | 31 |
| | HIP-9FL-KKK | KKKVKKIKAFVEQVANVVLYSSDYKKK | 32 |
| | HIP-9K1 | AFVEQVANVVL | 33 |
| | HIP-9K1-KKK | KKKAFVEQVANVVLKKK | 34 |
| HIP-17GN | HIP-17GN | VIGLTFRRDLYFSRVQVYPPVG | 35 |
| | HIP-17GN-KKK | KKKVIGLTFRRDLYFSRVQVYPPVGKKK | 36 |
| | HIP-17J | LTFRRDLYFSRVQVY | 37 |
| | HIP-17J-KKK | KKKLTFRRDLYFSRVQVYKKK | 38 |
| | HIP-17K1 | TFRRDLYFSRVQ | 39 |
| | HIP-17M1 | RRDLYFSRVQ | 40 |
| HIP-12AK | HIP-12AK | IDRTVLGILVSYQIKVKLTVSGFLG | 41 |
| | HIP-12AK-KKK | KKKIDRTVLGILVSYQIKVKLTVSGFLGKKK | 42 |
| | HIP-12E | VLGILVSYQIKVKLT | 43 |
| | HIP-12E-KKK | KKKVLGILVSYQIKVKLTKKK | 44 |
| | HIP-12G1 | GILVSYQIKVK | 45 |
| | HIP-12G1-KKK | KKKGILVSYQIKVKKKK | 46 |

In one aspect the peptide is selected from:

KKKVIFKKISRDKSVTIYLGKKK (SEQ ID No. 15)

RERRGIALDGKIKHE (SEQ ID No. 19)

LTKTLTLLPLLANNRERR (SEQ ID No. 25)

KKKAFVEQVANVVLKKK (SEQ ID No. 34)

KKKVIGLTFRRDLYFSRVQVYPPVGKKK (SEQ ID No. 36)

KKKGILVSYQIKVKKKK (SEQ ID No. 46)

In one aspect the peptide has at least 25%, 30%, 35%, 40%, 45%, 50%, 55%, 60%, 65%, 70%, 75%, 80%, 85%, 90%, 95% or 100% sequence identity to any one of SEQ ID NOs:1 to 9. In a preferred aspect the peptide has at least 80%, 90%, 95%, 97% or 99% sequence identity to any one of SEQ ID NOs:1 to 46.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4: 1-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are also useful for this purpose. Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9).

Multiple sequence alignments and percent identity calculations may be determined using the standard BLAST parameters, (using sequences from all organisms available, matrix Blosum 62, gap costs: existence 11, extension 1).

Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

Thus included in the scope of the invention are variants of the stated or given sequences, as long as the variant retains the functional activity of the parent i.e. the variants are functionally equivalent, in other words they have or exhibit an activity of the parent peptide as defined herein. Such variants may comprise amino acid substitutions, additions or deletions (including truncations at one or both ends) of the parent sequence e.g. of one or more e.g. 1 to 14 amino acids.

Also included are functionally-equivalent derivatives in which one or more of the amino acids are chemically derivatised, e.g. substituted with a chemical group.

Thus, the peptides of the invention can comprise portions or fragments of SEQ ID NOs 1-46, provided that the peptide retains the required activity. Portions or fragments of SEQ ID NOs 1-46 may for example be from 6 to 14 residues in length, e.g. 6, 7, 8, 9, 10, 11, 12 or 13 residues in length.

The peptide of the present invention may comprise between 8 and 30 amino acids, for example 8 to 25 amino acids, 8 to 20 amino acids, 8 to 15 amino acids or 8 to 12 amino acids. In one aspect the peptide of the present invention may thus be 8, 9, 10, 11, 12, 13, 14, 15, 16, 17, 18, 19, 20, 21, 22, 23, 24, 25, 26, 27, 28, 29 or 30 amino acids in length.

A peptide composition according to the invention may comprise the amino acid sequences according to the invention as described herein. In one aspect the peptide composition comprises only the amino acid sequences according to the invention as described herein, i.e. it does not comprise additional peptides other than those according to the invention.

The peptides of the invention may be formulated into the composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic acid. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Apitopes

In an adaptive immune response, T lymphocytes are capable of recognising epitopes of a protein antigen. APCs take up protein antigens and degrade them into short peptide fragments. A peptide may bind to a major histocompatibility complex (MHC) inside the cell and be carried to the cell surface. When presented at the cell surface in conjunction with an MHC molecule, the peptide may be recognised by a T cell (via the T cell receptor (TCR), in which case the peptide is a T cell epitope.

An epitope is thus a peptide derivable from an antigen which is capable of binding to the peptide-binding groove of an MHC molecule and being recognised by a T cell.

The minimal epitope is the shortest fragment derivable from an epitope, which is capable of binding to the peptide-binding grove of an MHC class I or II molecule and being recognised by a T cell. For a given immunogenic region, it is typically possible to generate a "nested set" of overlapping peptides which act as epitopes, all of which contain the minimal epitope but differ in their flanking regions.

By the same token, it is possible to identify the minimal epitope for a particular MHC molecule: T cell combination by measuring the response to truncated peptides. For example, if a response is obtained to the peptide comprising residues 1-15 in the overlapping library, sets which are truncated at both ends (i.e. 1-14, 1-13, 1-12 etc. and 2-15, 3-15, 4-15 etc.) can be used to identify the minimal epitope.

The present inventors have previously determined that there is a link between the capacity of a peptide to bind to an MHC molecule and be presented to a T cell without further processing, and the peptide's capacity to induce tolerance in vivo (WO 02/16410). If a peptide is too long to bind the peptide binding groove of an MHC molecule without further processing (e.g. trimming), or binds in an inappropriate conformation then it will not be tolerogenic in vivo. If, on the other hand, the peptide is of an appropriate size and conformation to bind directly to the MHC peptide binding groove and be presented to a T cell, then this peptide can be predicted to be useful for tolerance induction.

It is thus possible to investigate the tolerogenic capacity of a peptide by investigating whether it can bind to an MHC molecule and be presented to a T cell without further antigen processing in vitro.

S-Ag apitopes (Antigen Processing-Independent epiTOPES) are capable of binding to a MHC class II molecule and stimulating a response from S-Ag specific T cells without further antigen processing. Such apitopes can be predicted to cause tolerance to S-Ag, following the rule-based method described in WO 16410.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations in peptide length are accommodated by a kinking in the peptide backbone, often at proline or glycine residues that allow flexibility.

Peptides which bind to MHC class II molecules are typically between 8 and 20 amino acids in length, more usually between 10 and 17 amino acids in length, and can be longer (for example up to 40 amino acids). These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

In a preferred embodiment, the peptide derived from S—Ag is capable of binding to an MHC class II molecule without further processing.

Portion

The peptide of the present invention may comprise all or a portion of the S-Ag-derived peptides shown as SEQ ID NOs 1-46.

The term "portion" refers to a peptide that is derived from SEQ ID NOs 1-46 and contains at least a minimal epitope, that is, the peptide is capable of binding to the peptide-binding grove of an MHC class II molecule, being recognised by a T cell and inducing tolerance.

Solubility

Solubility may be an important consideration in peptide-mediated tolerance induction.

The present inventors have found that solubility may be improved by incorporation of additional amino acids which may be Glycine (G), Lysine (K) and/or Glutamic acid (E) at both N and C termini.

In one aspect, a peptide according to the invention may have, for example, one, two or three additional amino acids at the N and/or C termini. The additional amino acids may be selected from Glycine (G), Lysine (K) and/or Glutamic acid (E). Different combinations of these amino acids may be added to the peptides according to the invention.

For example, a peptide according to the invention may have one, two or three Lysine (K) residues at both N and C termini.

A peptide according to the invention may have one, two or three Glycine (G) residues at both N and C termini.

A peptide according to the invention may have one, two or three Glutamic acid (E) residues at both N and C termini.

In one aspect a peptide according to the invention may have one Glycine and one Lysine residue at both N and C termini.

In one aspect a peptide according to the invention may have one Glycine and two Lysine residues at both N and C termini.

In one aspect a peptide according to the invention may have one Glutamic acid and one Lysine residue at both N and C termini.

In one aspect a peptide according to the invention may have one Glutamic acid and two Lysine residues at both N and C termini.

In one aspect the peptide may have a Glycine spacer at both ends, followed by combinations of two additional amino acids which may be Lysine (K) and/or Glutamic acid (E) at both N and C termini. The possible combination at a given terminus may therefore be GKK, GKE, GEK or GEE.

The peptide may have the general formula:
XXG—parent peptide—GXX

In one aspect, a peptide according to the invention may have three additional Lysine (K) residues at both N and C termini.

Modified peptides according to the present invention may therefore have 6 additional amino acids (3 at each end) than the parent peptides.

The peptides of the present invention may alternatively have the general formula:
KKK—parent peptide—KKK
KK—parent peptide—KK
K—parent peptide—K
GK—parent peptide—KG
GKK—parent peptide—KKG
EK—parent peptide—KE
EKK—parent peptide—KKE
GKE—parent peptide—EKG
GEK—parent peptide—KEG The modified peptide may be more soluble that the parent (unmodified) peptide. The modified peptide may have 2, 3, 4, or 5-fold greater solubility than the parent peptide. The peptide may be soluble at concentrations of up to 0.5 mg/ml, 1 mg/ml, or 5 mg/ml.

In one aspect of the invention the peptide may be a modified form of one of the following peptides:

```
VIFKKISRDKSVTIYLG (SEQ ID NO: 14)

VIGLTFRRDLYFSRVQVYPPVG (SEQ ID NO: 35)

GILVSYQIKVK (SEQ ID NO: 45)

AFVEQVANVVL (SEQ ID NO: 33)
```

As discussed herein, the modified peptides of the present invention may have 2, 4 or 6 additional amino acids (1, 2 or 3 at each end) than the parent peptides.

In one aspect the modification is the inclusion of KKK at both the N and C termini.

The modified peptides may have the sequence:

```
                                    (SEQ ID NO: 34)
KKKAFVEQVANVVLKKK (SEQ ID NO: 46)
KKKGILVSYQIKVKKKK (SEQ ID NO: 36)
KKKVIGLTFRRDLYFSRVQVYPPVGKKK (SEQ ID NO: 15)
KKKVIFKKISRDKSVTIYLGKKK
```

The modified peptide may be more soluble that the parent (unmodified) peptide. The modified peptide may have 2, 3, 4, or 5-fold greater solubility than the parent peptide. The peptide may be soluble at concentrations of up to 0.5 mg/ml, 1 mg/ml, 5 mg/ml or higher, for example 8 mg/ml. In one aspect the modified peptide may be soluble at a concentration of 4 mg/ml.

S-Arrestin

S-arrestin (also known as retinal arrestin, S-antigen or S-Ag)

S-arrestin is a soluble photoreceptor protein expressed in the retina and the pineal gland. It is known to be involved in desensitization of the photoactivated transduction cascade, and was first isolated from its binding to activated rhodopsin. The crystal structure shows two domains of anti-parallel β-sheets joined by a hinge region as well as a short α-helix at the back of the amino terminal fold.

The light-activated form of the visual pigment rhodopsin (Rh*) interacts with the retinal G protein transducin, thereby initiating the exchange of a GDP molecule for GTP at the alpha-subunit of transducin. In its GTP-binding form transducin dissociates from Rh*, and activates a cyclic GMP phosphodiesterase (PDE), by binding to its two inhibitory subunits PDEγ. The result is a rapid decline in the concentration of the internal transmitter cyclic GMP. Because the interaction of Rh* and transducin takes only about 1 ms, a single Rh* can subsequently interact with hundreds of transducin molecules. The turnover number for PDE can be in the order of several thousand hydrolysed cGMP per PDE per second. Thus for a limitation of the light response as well as for a fast recovery, a rapid and effective elimination of Rh* is essential, before it can activate too many PDE molecules. This inactivation of Rh* is accomplished in two steps: phosphorylation of Rh* reduces its ability to catalyse the nucleotide exchange of transducin and subsequent binding of arrestin to P-Rh* completely shields it from further interaction with transducin.

The amino acid sequence of mature human S-Ag is given below (SEQ ID No. 47).

```
         10         20         30         40
MAASGKTSKS EPNHVIFKKI SRDKSVTIYL GNRDYIDHVS 50         60         70         80
QVQPVDGVVL VDPDLVKGKK VYVTLTCAFR YGQEDIDVIG 90        100        110        120
LTFRRDLYFS RVQVYPPVGA ASTPTKLQES LLKKLGSNTY 130        140        150        160
PFLLTFPDYL PCSVMLQPAP QDSGKSCGVD FEVKAFATDS 170        180        190        200
TDAEEDKIPK KSSVRLLIRK VQHAPLEMGP QPRAEAAWQF 210        220        230        240
FMSDKPLHLA VSLNKEIYFH GEPIPVTVTV TNNTEKTVKK 250        260        270        280
IKAFVEQVAN VVLYSSDYYV KPVAMEEAQE KVPPNSTLTK 290        300        310        320
TLTLLPLLAN NRERRGIALD GKIKHEDTNL ASSTIIKEGI 330        340        350        360
DRTVLGILVS YQIKVKLTVS GFLGELTSSE VATEVPFRLM 370        380        390        400
HPQPEDPAKE SYQDANLVFE EFARHNLKDA GEAEEGKRDK

NDVDE
```

Uveitis

Clinically, uveitis is commonly classified as one of the following based on the part of the eye which is primarily affected: anterior uveitis, intermediate uveitis, posterior uveitis or panuveitis.

Anterior uveitis is the most common form of uveitis, and includes iridocyclitis and iritis. Iritis is the inflammation of the anterior chamber and iris, while iridocyclitis includes inflammation in the ciliary body.

Intermediate uveitis (pars planitis) commonly refers to vitritis—inflammation of cells in the vitreous cavity, associated with deposition of inflammatory material on the pars plana.

Posterior uveitis (chorioretinitis) is the inflammation of the retina and choroid regions.

Panuveitis uveitis is a general term referring to inflammation affecting all layers of the uvea.

Uveitis can also be classified as either infectious or non-infectious, with uveitis related to autoimmune diseases (i.e. primarily non-infectious) being more common in developed countries. The common animal models used to study uveitis are also driven by autoimmunity, showing a clear association between the two. It is predicted that 25-30% of uveitis is associated with systemic autoimmune or autoinflammatory diseases.

In one aspect of the invention the uveitis is non-infectious uveitis.

Tolerance

T cell epitopes play a central role in the adaptive immune response to any antigen, whether self or foreign. The central role played by T cell epitopes in hypersensitivity diseases (which include allergy and transplant rejection) has been demonstrated through the use of experimental models. It is possible to induce autoimmune or allergic diseases by injection of synthetic peptides (based on the structure of T cell epitopes) in combination with adjuvant.

By contrast, it has been shown to be possible to induce immunogenic tolerance towards particular antigens by administration of peptide epitopes in soluble form. Administration of soluble peptide has been demonstrated as an effective means of inhibiting disease in experimental autoimmune encephalomyelitis (EAE—a model for multiple sclerosis (MS)) (Metzler and Wraith (1993) Int. Immunol. 5:1159-1165; Liu and Wraith (1995) Int. Immunol. 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues. This is controlled to a large extent by negative selection of high-affinity T lymphocytes in the thymus (central tolerance). However, not all self antigens are expressed in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) Immunological Reviews 169:123-137. See also Wraith (2016) Nature 530: 422-423.

Available data suggests that uveitis can result from autoreactive T cells being generated from retinal proteins, including S-Ag, driving inflammation and causing chronic disease. The composition of the present invention is capable of inducing tolerance to self-antigens such as S-Ag, such that when administered to a subject, it may reinstate tolerance to the S-Ag protein and curtail the pathogenic immune response.

Composition

The composition of the present invention may be for prophylactic or therapeutic use.

When administered for prophylactic use, the composition may reduce or prevent the generation of an immune response to S-Ag. The level of immune response is less than would be obtained if the patient had not been treated with the composition. The term "reduce" indicates that a partial reduction in immune response is observed, such as a 50%, 70%, 80% or 90% reduction in the response that would have been observed if the patient had not been treated with the composition (or in the response observed in an untreated patient over the same time-period). The term "prevent" indicates that no appreciable immune response to S-Ag is observed.

When administered for therapeutic use, the composition may suppress an already on-going immune response to S-Ag. The term "suppress" indicates a reduction in the level of an on-going immune response, compared to the level before peptide treatment, or the levels which would have been observed at the same time point had the treatment not been given.

Treatment with the composition of the present invention may cause a reduction in level of any or all of the following:
  i) S-Ag autoantibodies
  ii) proinflammatory CD4+ T cells specific for S-Ag
  iii) B cells secreting S-Ag autoantibodies.

Detection of all of the factors can be carried out by techniques known in the art, such as ELISA, flow cytometry etc.

Treatment with the composition of the present invention may also or alternatively cause anergy in CD4+ T cells specific for S-Ag. Anergy can be detected by, for example, subsequent challenge with S-Ag in vitro. Treatment with the composition of the present invention may cause generation of antigen-specific regulatory T cells, for example characterised by transcription factors c-Maf and NFIL3, and negative co-stimulatory molecules LAG-3, TIGIT, PD-1 and TIM-3 (see Burton et al. Nature Communications (2014) Article number 4741).

Formulation

The composition may by prepared as an injectable, either as liquid solution or suspension; solid form suitable for solution in, or suspension in, liquid prior to injection may also be prepared. The preparation may also be emulsified, or the peptides encapsulated in liposomes. The peptide may alternatively be encapsulated in a carrier or bound to the surface of a carrier, for example a nanoparticle. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents. Buffering salts include phosphate, citrate, acetate. Hydrochloric acid and/or sodium hydroxide may be used for pH adjustment. For stabilisation, disaccharides may be used such as sucrose or trehalose.

In the composition, the relative ratio of the peptides may be approximately 1:1. Alternatively the relative ratios of each peptide may be altered, for example, if it is found that one peptide works better than the others in particular HLA types.

After formulation, the composition may be incorporated into a sterile container which is then sealed and stored at a low temperature, for example 4° C., or it may be freeze-dried.

Conveniently, the composition is prepared as a lyophilised (freeze-dried) powder. Lyophilisation permits long-term storage in a stabilised form. Lyophilisation procedures are well known in the art, see for example http COLON SLASH SLASH www.devicelink.com/ivdt/archive/97/01/006.html Bulking agents are commonly used prior to freeze-drying, such as mannitol, dextran or glycine.

The composition may be administered in a convenient manner such as by the oral, intravenous (where water soluble), intramuscular, subcutaneous, sublingual, intranasal, intradermal or suppository routes or implanting (e.g. using slow release molecules).

The composition may advantageously be administered via intranasal, subcutaneous or intradermal routes.

The peptide or composition as described herein is typically administered in an "effective amount"; that is, an amount effective to elicit any one or more inter alia of a therapeutic or prophylactic effect. Persons skilled in the art would be able, by routine experimentation, to determine an effective, non-toxic amount to include in a pharmaceutical composition or to be administered for the desired outcome. In general, the peptide or composition as disclosed herein can be administered in a manner compatible with the route of administration and physical characteristics of the recipient (including health status) and in such a way that it elicits the desired effect(s) (i.e. therapeutically effective and/or protective). For example, the appropriate dosage of a composition may depend on a variety of factors including, but not limited to, a subject's physical characteristics (e.g., age, weight, sex), and other factors that may be recognized by persons skilled in the art. Other illustrative examples of general considerations that may be considered when determining, for example, an appropriate dosage of the compositions are discussed by Gennaro (2000, "Remington: The Science and Practice of Pharmacy", 20th edition, Lippincott, Williams, & Wilkins; and Gilman et al., (Eds), (1990), "Goodman And Gilman's: The Pharmacological Bases of Therapeutics", Pergamon Press).

The peptide and composition of the invention may be used to treat a human subject. The subject may have uveitis. The subject may have S-Ag autoreactive T cells.

The subject may be an HLA-haplotype which is associated with a predisposition to produce excessive T cells specific for S-Ag. Methods for determining the HLA haplotype of an individual are known in the art. In one aspect the subject has an HLA gene selected from the following: A29, B51, B27, DR8, DR4, DP5, DR4, DQA3, DR3, DR2, DR51, and DR17 (see Mattapallil et al. J Immunol 2011, 187:1977-1985).

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Kit

Peptides derived from S—Ag may be administered together, in the form of a mixed composition or cocktail. However, there may be circumstances in which it is preferable to provide the peptides separately in the form of a kit, for simultaneous, separate, sequential or combined administration.

For example, the kit may comprise the peptides in separate containers. The contents of the containers may or may not be combined prior to administration.

The kit may also comprise mixing and/or administration means (for example a vapouriser for intranasal administration; or a syringe and needle or other medical device for subcutaneous/intradermal dosing). The kit may also comprise instructions for use.

The pharmaceutical composition or kit of the invention may be used to treat and/or prevent a disease, such as uveitis as discussed herein.

In particular, the composition/kit may be used to suppress or prevent the production of S-Ag-specific CD4+ T cells (or S-Ag autoantibodies) in vivo. The composition/kit may be used to treat and/or prevent uveitis in a subject.

Model for Analysing In Vivo Peptide Presentation

The present invention also encompasses a model for in vivo peptide presentation. As demonstrated in the present Examples (see e.g. FIG. 14), As such, in one aspect the invention encompasses a method for ex vivo determination of in vivo peptide presentation, wherein said method comprises:
  (i) co-culturing CD11c$^+$ cells from a mouse which has been injected with said peptide with CD4$^+$ cells specific for said peptide
  (ii) analysing the supernatant co-culture for CD4$^+$ T cell activation or alternatively determining T cell proliferation.

CD4$^+$ T cell activation and/or proliferation may indicate presentation of the peptide by an MHC molecule.

In one aspect analysis of CD4$^+$ T cell activation is performed by assessing the level of IFN-γ in the supernatant. Methods for analysing the level of IFN-γ are known in the art, for example, ELISA methods.

In one aspect the mouse is a DR3tg or DR2tg mouse. In one aspect the mouse has been injected with about 100 µg of peptide, for example by subcutaneous injection. In one aspect the CD11c$^+$ cells are harvested from the spleen of the mouse.

EXAMPLES

Example 1—Identification of T-Cell Epitopes in S-Ag

In silico methodology was used to predict regions containing T-cell epitopes in S-Ag, and resulted in the determination of SEQ ID Nos 1-9, as described below.

Calculation of Allele Frequencies

Allele frequencies were calculated from the allele frequency database (http COLON SLASH SLASH www.allelefrequencies.net). The allele frequency database consist of several thousand individual studies from various geographic locations and ethnic populations, with each study focusing on one specific ethnic or geographic population. The size of the cohort analysed and location varies greatly between studies, however the largest studies originate from Europe and North America. The frequencies in a general World Population were calculated as an average of allele frequencies from the individual studies weighted by the number of test-subjects. To avoid bias towards large studies, the number of test subjects in studies with more than 5000 was set to 5000. This ensures a lower bias in the region specific population, however the world average is still biased towards the European and the North American population. In the calculated world average population, studies on North American populations have a weight of 52.7%, Europe 25.3%, North East Asia 9.2%, South East Asia 5.9%, South Central America 1.7%, Oceania 1.3%, Western Asia 1.3%, Sub-Saharan Africa 1.0%, South Asia 0.7%, North Africa 0.6%, Australia 0.1%.

MHC II Peptide Binding Predictions

State of the art in silico prediction tools; NetMHCII and NetMHCIIpan were employed for identification of potential T-helper cell epitopes for the most prevalent HLA-alleles, i.e. Alleles found in more than 1% of the population. NetMHCII and NetMHCIIpan predicts interaction between MHC Class II molecules, encoded by the HLA loci in humans, and protein sub-15-mer. The tools are developed based on thousands of peptide-MHC interactions measurements and predicts IC50 values for a given 15-mer peptide and HLA-allele. However, a % Rank value instead of the predicted IC50 values was used to standardize predictions across MHC alleles as recommended by the IEDB (www.iedb.org). The % Rank value indicates the significance of the interaction value compared to interaction of random human derived peptides i.e. a % Rank value of 10 means that the interaction value is in the top 10% of the strongest measured interactions. The lower the rank values the higher the likelihood of a peptide binding to the given MHC molecule.

Here, the algorithms NetMHCII2-2 (for DP and DQ) NetMHCIIpan-2.1 were used as described in Nielsen et al. (2010) *Immunome Res* 6, 9 and Nielsen and Lund (2009) *BMC Bioinformatics* 10, 296. Each protein sequence was analysed for sub-15mer MHC II binding peptides restricted to each of the HLA alleles in Table 4 by decomposing the protein to overlapping 15-mer peptides.

Risk Score Calculation

Only peptides predicted with a rank score of less than 10 were considered as potential MHC II binders. For different peptides predicted to bind to the same HLA allele and having identical predicted binding cores, only the peptide with the strongest predicted binding affinity was considered.

A score for each sub-15mer peptide was calculated as the summed population frequency of HLA molecules predicted to bind the given peptide (Equation 1). This score is referred to as risk score, however it reflects the population coverage of HLA molecules predicted to bind to each sub-15mer peptide, and thus does not reflect clinical immunogenicity.

Risk score $$S_p = \frac{\sum_{a \in HLA} r_p \leq T_{epi} \cdot f_a}{\sum_{a \in HLA} f_a}$$ Equation 1

Where $S_P$ is the 15-mer peptide starting at position p, $r_p$ the predicted rank score of the peptide starting at position p binding to allele a. $f_a$ is the allele frequency for allele a, $T_{epi}$ is the binding threshold for considering a peptide a potential epitope (i.e. 10% rank). The maximum value of the risk score depends on the coverage of HLA alleles of the investigated population. However the theoretical max is 1, which is achieved when all overlapping 15-mers for a given position are predicted to be bind to $S_P$.

SEQ ID Nos: 1-9 were found through evaluating the most potent potential epitopes, defined as having a risk score above 0.4. A risk score of 0.4 corresponds to approximately two standard deviations above the mean risk value for S-Ag.

Example 2—Identification of S-Ag Apitopes

Apitopes are identified within the identified regions.

Example 3—Solubility of Identified Apitopes

The solubility of potential apitopes from S—Ag are determined by visual observations and turbidity measurement by UV spectrophotometry at 280 nm. The solubility of the peptides can be modified by adding amino acids 'GKK' or 'KKK' (or similar) on both the C- and N-terminus of the sequence. Modifications that may be suitable are described in WO2014/072958 (which is hereby incorporated by reference).

Example 4—Ex Vivo Tolerance Assay

The ability of the S-Ag apitopes to inhibit the immune response is investigated in healthy HLA-DRB1*DR3 mice ex vivo. Mice are pretreated with different apitopes according to the following schedules:

Mice are injected subcutaneously in the flanks with S-Ag peptides (100 μg/injection) or PBS at day −8, −6, −4 (high dose schedule). Alternatively, mice are injected using a dose escalation schedule, wherein e.g. X μg of peptide are administered, followed by 10×μg, then 100×μg then 1000×μg. For example on day 0, the mice may be injected subcutaneously in the base of the tail with 50-100 μg antigen/CFA (S-Ag or the native sequence of the tolerogenic peptide). Ten days after immunization, the draining LNs and spleens are harvested. Proliferation assay are then performed as described below.

Proliferation assay After 72 hours, 60 μL of cell supernatant are harvested and frozen. 20 μL/well of tritiated thymidine (PerkinElmer, Zaventem, Belgium) are then added to the cells to obtain a final concentration of 1 μCi/well. The cells are incubated at 37° C., and after 16 h, plates are frozen. Thawed plates are harvested and read with β-counter (Wallac 1450 Microbeta Trilux Liquid Scintillation Counter) to assess the cell proliferation.

Example 5—Identification and Analysis of S-Ag Apitopes

The S-arrestin (SAg) was subdivided in 28 shorter peptides and screened to determine immunogenic regions. Based on in silico MHC class II binding prediction tools (described above), several immunodominant regions were identified as discussed above. Six peptides were discovered as apitopes within five SAg regions. Solubility being an important parameter in the tolerising ability of the peptides, it was assessed and improved when needed by adding N- and C-terminal amino acids to the peptides (i.e. KKK). Ex vivo tolerance experiments confirmed the peptide's ability to induce tolerance towards SAg and/or the native peptide. Moreover, the ability to be presented by MHC class II in an in vivo setting was tested and the six peptides were found to be successfully picked up by antigen presenting cells (i.e. dendritic cells) and presented to CD4+ T cells.

Materials & Methods

Mice

DR3tg mice were bred under specific pathogen-free conditions externally at Charles River, UK, or at Innoser, Netherlands. The DR3tg strain was originally created by Strauss et al (Strauss et al, 1994, Immunogenetics 3, 104-108). In brief, the genomic constructs used were a 6 kb NdeI fragment of a HLA-DRA genomic clone in pUC 13 and a 24 kb ClaIxSalI fragment of cos 4.1, a cosmid (pTCF) containing the B gene of DRB1*0301. A solution containing 1-2 μg/mL of each construct was used for co-injection into fertilised eggs from (C57BL/6×DBA/2) F1 donors mated with C57BL/6 males. The offspring were later bred into the IA-beta knockout B6; 129S2-H2dlAb1-Ea/J lacking mouse MHC class II molecule expression. These DR3tg mice express the HLA-DRB1*0301 molecule but not the mouse MHC-II molecule. The mice were maintained by backcrossing to C57BL/6 and to B10.Q. Transgenic mice were identified by Southern blot analysis of tail DNA digested with EcoRI and probed with a 1.35 kb BamHI fragment of the DRA cDNA and a 1.25 kb BamHI fragment of the DRB1*0301 cDNA. DR3tg mice were used for these experiments as it has been suggested that this MHC class II molecule is associated with an increased risk for individuals to develop uveitis disease.

DR2tg mice were bred under specific pathogen-free conditions externally at Charles River, UK, or at Innoser, Netherlands. HLA-DR2 transgenic (DR2tg) mice were originally obtained from Lars Fugger (Madsen et al., 1999). In brief, DRα and DRβ chain cDNAs (DRA*0101 and DRB1*1501) were expressed by using the pDOI-5 expression vector which contains a mouse MHCII promotor. The constructs were injected into fertilised eggs from (DBA/2× C57BL/6) F1 matings. The mice were backcrossed into the IA-beta knockout C57BL/6 genetic background (AB0 mice) lacking mouse MHC class II molecule expression. The DR2tg mice express the HLA-DRB1*1501 molecule but not the mouse MHC molecule.

Animal studies were approved by the 'Ethical Committee for Animal experiments' (ECD) at Hasselt University and performed with the highest standards of care in a pathogen-free facility.

Antigens

All single peptides were synthesized by Severn Biotech (Kidderminster, UK) and stored at a stock solution of 20 mg/ml in DMSO (Sigma-Aldrich) at −80° C. The peptides were synthesized with an N-terminal free amine and a C-terminal amide. Human SAg (S-arrestin) was produced in HEK293F cells (QBiologicals, Eurofins Amatsigroup, Ghent, Belgium).

Antigen Processing Independent Presentation System (APIPS) Assay

Antigen-specific clones or TCL were tested for their reactivity to the peptides, presented by fixed or not fixed (fresh) cells (VAVY or MGAR) (=APCs). $5 \times 10^4$ cells from the individual clones were cultured with 10 μg/ml peptide and $5 \times 10^4$ fixed or fresh APCs. In the case of TCL, $5 \times 10^4$ cells were cultured with 10 μg/ml and 25 μg/ml peptide and $2.5 \times 10^4$ fixed or fresh APCs. To fixate APCs, cells were incubated with 0.5% paraformaldehyde (Merck, Darmstadt, Germany) (pH7) for 5 min at room temperature (RT). The fixation reaction was stopped by adding 0.4M glycine (Sigma-Aldrich) and washing the cells in RPMI-10% FCS. Additionally, reactivity towards human SAg protein (QBiologicals, Eurofins Amatsigroup, Ghent, Belgium) was measured to identify cryptic epitopes. After 24 h or 48 h, antigen-induced IFN-γ or IL-2 production (respectively) was measured by ELISA (R&D Systems, Abingdon, UK).

Ex Vivo Tolerization Experiment

DR3tg or DR2tg mice were injected subcutaneously in the flank region with 0.1 μg, 1 μg and 10 μg of peptide on days −15, −13 and −11 respectively, followed by 3 injections of 100 μg peptide on days −8, −6 and −4 (dose escalation schedule). On day 0, the mice were immunised subcutaneously in the base of the tail with 50 μg antigen (parental peptide) emulsified in CFA (peptide/CFA). Ten days after immunisation, draining lymph nodes (LN) and spleens were harvested. LN cells and splenocytes were isolated and cultured in X-vivo 15 medium (supplemented with 2 mM L-glutamine, 50 U/mL penicillin and 50 U/mL streptomycin; Lonza) in 96-well flat bottom plates. To investigate antigen-induced cell proliferation, $0.5 \times 10^6$ cells/well were cultured (200 μl/well) for 72 hours with different antigen concentrations (0-25 μg/ml) or with 12.5 μg/ml purified protein derivative (PPD; priming control; Statens serum institut, Copenhagen, Denmark). After 72 hours, supernatant was harvested and stored at −80° C. until further analysis. IFN-γ concentrations in supernatants were assessed by cytokine ELISA (R&D Systems, Abingdon, UK) to measure cell activation.

Set-Up of T Cell Line (TCL)

DR3tg or DR2tg mice were immunised subcutaneously in the base of the tail with 50 μg peptide emulsified in CFA (peptide/CFA). Ten days after immunisation, draining lymph nodes (LN) and spleens were harvested. LN cells and splenocytes were isolated and CD4$^+$ T cells were isolated by negative selection using Magnisort Mouse CD4 Isolation kit (ThermoFisher Scientific) according to the manufacturer's instructions. Irradiated (3000 rad) splenocytes were used as antigen-presenting cells (APC). $5 \times 10^6$ APC+$2.5 \times 10^6$ CD4$^+$ T cells were cultured in X-vivo 15 medium (supplemented with 2 mM L-glutamine, 50 U/mL penicillin and 50 U/mL streptomycin; Lonza) in 6-well plates in the presence of 0.1; 1; 2.5 or 5 μg/ml of peptide. At day 4, 20 U/ml of rIL-2 (R&D Systems, Abingdon, UK) was added. At day 7, TCL cells were counted and cultured with fresh APC, peptides and IL-2, all at the same concentrations as above. On day 10, 20 U/ml of rIL-2 was added. On day 14, TCL cultures were used as such, or CD4$^+$ cells were selected.

In Vivo Presentation Experiment

DR3tg or DR2tg mice were injected with 100 μg of peptide in 100 μl PBS subcutaneously (s.c.) in the flank. Control animals received a s.c. injection of 100 μl PBS. After 2 hours, spleens were harvested and single-cell suspensions were made. CD11c$^+$ cells were positively selected using CD11c microbeads according to the manufacturer's instructions (Miltenyi Biotec, Bergisch Gladbach, Germany). Average purities of >92% were reached. $5 \times 10^4$ CD11c$^+$ cells were co-cultured with $5 \times 10^4$ CD4$^+$ cells in round bottom 96-well plates in X-vivo 15 medium (supplemented with 2 mM L-glutamine, 50 U/mL penicillin and 50 U/mL streptomycin; Lonza). These CD4$^+$ cells were isolated from peptide-specific T cell lines (see above) by positive selection using CD4$^+$ microbeads according to the manufacturer's instructions (Miltenyi Biotec). After 48 hours, supernatant of these co-cultures was collected and CD4$^+$ T cell activation was analysed by IFN-γ ELISA (R&D Systems, Abingdon, UK). In a parallel experiment, CD4$^+$ T cell responses towards peptide added in vitro were assessed to make sure the T cells recognize the peptides presented by the CD11c$^+$ cells.

Results

Results and Discussion

1. IDENTIFICATION OF T CELL EPITOPES WITHIN SAg

In silico methodology was used to predict regions containing T-cell epitopes in SAg, and resulted in the determination of SEQ ID Nos 1-9, as described previously.

Animal experiments were done to verify the predictions. Mice that were immunized with SAg (or fragments of it) were tested for their capacity to elicit an immune response when probed with the whole protein or parts of it. One of such fragments is shown in FIG. 1, where it can be seen that mice that were previously immunized with peptide HIP-115 develop an immune response against it, while control mice don't (black). This response can be observed in secondary lymphoid organs, namely spleen (FIG. 1A) and lymph nodes (LN; FIG. 1B).

2. IDENTIFICATION OF APITOPES WITHIN IMMUNOGENIC FRAGMENTS

Apitopes (Antigen Processing-Independent epiTOPES) are capable of binding to an MHC molecule and stimulating a response from SAg specific T cells without further antigen processing. Such apitopes can be predicted to cause tolerance to SAg, following the rule-based method described in WO 02/16410. FIGS. 2 to 6 show the identification of apitopes within the sequences that were previously identified as immunogenic.

FIG. 2 focuses on the HIP-115 region (SEQ ID No 1). The ability of both a hybridoma clone (FIG. 2A) and a T cell line (FIG. 2B) to respond to peptides that were picked up and presented by fresh or fixed antigen presenting cells (APC) indicates that HIP-115, HIP-115NE, HIP-115NE1, HIP-115NE2, HIP-115NE3 and HIP-115NE3-KKK behave as apitopes.

FIG. 3 focuses on the HIP-241125 region (SEQ ID No 7). In this case, different apitopes were identified depending on whether the response to peptide was assessed using hybridomas (FIG. 3A) or T cell line (FIG. 3B). HIP-11AC, HIP-11AC1 and HIP-11B behave as apitopes (FIG. 3A), and so do HIP-24DG, HIP-24HM, HIP-24HM2, HIP-24HM3 and HIP-241125 itself.

FIG. 4 focuses on the HIP-9FL region (SEQ ID No 9). Peptides HIP-9FL, HIP-9FL-KKK and HIP-9K1-KKK behave as apitopes.

FIG. 5 focuses on the HIP-17GN region (SEQ ID No 3). Peptides HIP-17GN, HIP-17GN-KKK, HIP-17J, HIP-17J-KKK and HIP-17K1-KKK behave as apitopes.

FIG. 6 focuses on the HIP-12AK region (SEQ ID No 8). Peptides HIP-12G1, HIP-12G1-KKK and HIP-12E-KKK behave as apitopes.

3. T CELL TOLERANCE INDUCTION BY SINGLE PEPTIDES

To determine the tolerogenic effect of single peptides derived from the identified regions of SAg HIP-115NE3-KKK (FIG. 8), HIP-11B (FIG. 9), HIP-24DG (FIG. 10), HIP-9K1-KKK (FIG. 11), HIP-17GN-KKK (FIG. 12) and HIP-12G1-KKK (FIG. 13), transgenic mice were treated according to the dose escalation schedule (FIG. 7) with each one of the peptides.

For some of these peptides, the parental peptides were insoluble, and solubility is a critical parameter for them to work as a tolerogenic peptide. Several end-terminal modifications can be used and as example used here they were improved by addition of 3 lysines before and after the original peptide sequence (labelled as '-KKK' versions).

FIG. 8 shows how the soluble form of peptide HIP-115NE3 (HIP-115NE3-KKK) is capable of inducing tolerance against SAg in LN (FIG. 8A) and in spleen (FIG. 8B), amounting to 70% reduction in response to SAg when the highest dose of SAg was used for probing. Furthermore, HIP-115NE3-KKK induces tolerance against HIP-115 and HIP-115NE3 peptides in LN (FIG. 8C) and spleen (FIG. 8D); 55% and 65% reduction in response respectively at the highest concentrations of probing peptide.

FIG. 9 shows the tolerization induced by peptide HIP-11B against SAg in LN (FIG. 9A) and in spleen (FIG. 9B), and especially against HIP-11B itself in LN (FIG. 9C) and in spleen (FIG. 9D).

FIG. 10 shows the tolerization induced by peptide HIP-24DG against SAg in LN (FIG. 10A). There is some tolerization against HIP-24DG itself (FIG. 10B) and other peptides within the same region, namely HIP-24HM2 (FIG. 10C) and HIP-24HM3 (FIG. 10D), all results shown for LN.

FIG. 11 shows the tolerization induced by peptide HIP-9K1-KKK in LN against SAg (FIG. 11A). HIP-9FL and HIP-9K1-KKK (FIG. 11B). Tolerance is also induced in spleens against SAg (FIG. 11C) and to HIP-9K1-KKK itself (FIG. 11D).

FIG. 12 shows the tolerization induced by peptides HIP-17GN-KKK and HIP-17J-KKK against SAg in spleen.

FIG. 13 shows the tolerization induced by peptide HIP-12G1-KKK against itself in LN (FIG. 13A) and in spleen (FIG. 13B).

4. IN VIVO PRESENTATION OF SINGLE PEPTIDES

Peptides were further investigated in order to assess their ability to bind MHC class II molecules present on APC. FIG. 14 shows the experimental design for such an experiment and detailed information can be found in the M&M section. Of note, solubility is an important parameter in this test as well.

In FIG. 15 the ability of HIP-115NE3 (insoluble peptide) and that of its soluble version, HIP-115NE3-KKK, to be picked up and presented by MHC II molecules present on dendritic cells (DC) upon sc. injection in an in vivo setting (DR3tg mice) was compared. As shown in the graph, HIP-115NE3-KKK is bound to the MHC II on DC in situ and presented to peptide-specific T cells after DC cell isolation. T cell activity response was measured by production of IFN-γ. In turn, the insoluble peptide was not able to cause this activation showing solubility to be a critical property for tolerogenic peptides.

In FIG. 16 the ability of HIP-24DG, HIP-24HM2 and HIP-24HM3 peptides (all soluble) to be picked up and presented by MHC II molecules present on dendritic cells (DC) upon injection in an in vivo setting (DR3tg mice) was compared. As shown in the graph, HIP-24HM3 is presented by DC to T cells, which become activated and produce IFN-γ.

In FIG. 17 the ability of HIP-9K1 (insoluble peptide) and that of its soluble version, HIP-9K1-KKK, to be picked up and presented by MHC II molecules present on dendritic cells (DC) upon injection in an in vivo setting (DR2tg mice) was compared. As shown in the graph, HIP-9K1-KKK is presented by DC to T cells, which become activated and produce IFN-γ. In turn, the insoluble peptide was not able to cause this activation.

In FIG. 18 the ability of HIP-17GN-KKK and HIP-17J-KKK to be picked up and presented by MHC II molecules present on dendritic cells (DC) upon injection in an in vivo setting (DR3tg mice) was compared. As shown in the graph, HIP-17J-KKK is presented by DC to T cells, which become activated and produce IFN-γ. A certain degree of activation is also seen for HIP-17J-KKK.

5. CONCLUSIONS

We have evaluated the in silico identified regions and present functional examples of short sequences (peptides) located in the regions. The 7 peptides shown in the examples are all included within the SEQ ID Nos 1, 3, 7, 8 and 9 sequences. and show an ability to induce tolerance against SAg or fragments of it. In particular, we have used 3 tests:

APIPS, in vivo presentation test and in vivo tolerance induction. All 6 peptides (i) act as apitopes (i.e. are antigen processing independent epitopes), (ii) can be presented ex vivo to peptide specific T cells by MHCII molecules present on dendritic cells and (ii) are able to induce tolerance against SAg or fragments of it when administered using the escalating dose regime of treatment.

All publications mentioned in the above specification are herein incorporated by reference. Various modifications and variations of the described methods and uses of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, immunology or related fields are intended to be within the scope of the following claims.

The invention claimed is:

1. A peptide capable of binding to a major histocompatibility complex (MHC) molecule in vitro and being presented to a T cell without antigen processing,
   wherein said peptide comprises an amino acid sequence selected from the following:
   KKKVIFKKISRDKSVTIYLGKKK (SEQ ID NO: 15),
   an amino acid sequence having at least 80% identity to SEQ ID NO: 15, KKKAFVEQVANVVLKKK (SEQ ID NO: 34),
   an amino acid sequence having at least 80% identity to SEQ ID NO: 34, KKKVIGLTFRRDLYFSRVQVYPPVGKKK (SEQ ID NO: 36),
   an amino acid sequence having at least 80% identity to SEQ ID NO: 36, KKKGILVSYQIKVKKKK (SEQ ID NO: 46) and
   an amino acid sequence having at least 80% identity to SEQ ID NO: 46;
   or wherein said peptide consists of an amino acid sequence selected from the following:
   RERRGIALDGKIKHE (SEQ ID NO: 19) and
   LTKTLTLLPLLANNRERR (SEQ ID NO: 25).

2. A composition comprising a plurality of peptides, including one or more peptide(s) according to claim 1.

3. A method for suppressing the production of S-Ag-specific T cells in a subject, which comprises the step of administering the composition according to claim 2 to the subject.

4. A method for treating uveitis in a subject which comprises the step of administering the composition according to claim 2 to the subject.

5. A method for suppressing the production of S-Ag-specific T cells in a subject, which comprises the step of administering the peptide according to claim 1 to the subject.

6. A method for treating uveitis in a subject which comprises the step of administering the peptide according to claim 1 to the subject.

7. The peptide of claim 1 having an amino acid sequence selected from: KKKVIFKKISRDKSVTIYLGKKK (SEQ ID NO: 15), and an amino acid sequence having at least 80% identity to SEQ ID NO: 15.

8. The peptide of claim 1, wherein the amino acid sequence of the peptide consists of the sequence LTKTLTLLPLLANNRERR (SEQ ID NO: 25).

9. The peptide of claim 1 having an amino acid sequence selected from: KKKAFVEQVANVVLKKK (SEQ ID NO: 34), and an amino acid sequence having at least 80% identity to SEQ ID NO: 34.

10. The peptide of claim 1 having an amino acid sequence selected from: KKKVIGLTFRRDLYFSRVQVYPPVGKKK (SEQ ID NO: 36), and an amino acid sequence having at least 80% identity to SEQ ID NO: 36.

11. The peptide of claim 1 having an amino acid sequence selected from: KKKGILVSYQIKVKKKK (SEQ ID NO: 46) and an amino acid sequence having at least 80% identity to SEQ ID NO: 46.

12. The peptide of claim 1 having an amino acid sequence consisting of the amino acid sequence RERRGIALDGKIKHE (SEQ ID NO: 19).

* * * * *

```
                    SEQUENCE LISTING

<160> NUMBER OF SEQ ID NOS: 47

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ile Phe Lys Lys Ile Ser Arg Asp Lys Ser Val Thr Ile Tyr Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Lys Gly Lys Lys Val Tyr Val Thr Leu Thr Cys Ala Phe Arg Tyr
1               5                   10                  15

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide

<400> SEQUENCE: 3

Val Ile Gly Leu Thr Phe Arg Arg Asp Leu Tyr Phe Ser Arg Val Gln
1               5                   10                  15

Val Tyr Pro Pro Val Gly
            20

<210> SEQ ID NO 4
<211> LENGTH: 37
<212> TYPE: PRT
<213> ORGANISM: Artificial Sequence
<220> FEATURE:
<223> OTHER INFORMATION: Synthetic peptide

<400> SEQUENCE: 4

Glu Ser Leu Leu Lys Lys Leu Gly Ser Asn Thr Tyr Pro Phe Leu Leu
1               5                   10                  15

Thr Phe Pro Asp Tyr Leu Pro Cys Ser Val Met Leu Gln Pro Ala Pro
            20                  25                  30

Gln Asp Ser Gly Lys
        35

<210> SEQ ID NO 5
<211> LENGTH: 17
```

```
<212> TYPE: PRT
<213> ORGANISM: Artificial Sequence
<220> FEATURE:
<223> OTHER INFORMATION: Synthetic peptide

<400> SEQUENCE: 5

Ser Ser Val Arg Leu Leu Ile Arg Lys Val Gln His Ala Pro Leu Glu
1               5                   10                  15
Met

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide

<400> SEQUENCE: 6

Ala Glu Ala Ala Trp Gln Phe Phe Met Ser Asp Lys Pro Leu His Leu
1               5                   10                  15
Ala Val Ser Leu Asn Lys Glu Ile Tyr Phe
            20                  25

<210> SEQ ID NO 7
<211> LENGTH: 41
<212> TYPE: PRT
<213> ORGANISM: Artificial Sequence
<220> FEATURE:
<223> OTHER INFORMATION: Synthetic peptide

<400> SEQUENCE: 7

Leu Thr Lys Thr Leu Thr Leu Leu Pro Leu Leu Ala Asn Asn Arg Glu
1               5                   10                  15
Arg Arg Gly Ile Ala Leu Asp Gly Lys Ile Lys His Glu Asp Thr Asn
            20                  25                  30
Leu Ala Ser Ser Thr Ile Ile Lys Glu
        35                  40

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide

<400> SEQUENCE: 8

Ile Asp Arg Thr Val Leu Gly Ile Leu Val Ser Tyr Gln Ile Lys Val
1               5                   10                  15
Lys Leu Thr Val Ser
            20

<210> SEQ ID NO 9
<211> LENGTH: 29
<212> TYPE: PRT
<213> ORGANISM: Artificial Sequence
<220> FEATURE:
<223> OTHER INFORMATION: Synthetic peptide

<400> SEQUENCE: 9

Asn Thr Glu Lys Thr Val Lys Ile Lys Ala Phe Val Glu Gln Val
1               5                   10                  15
Ala Asn Val Val Leu Tyr Ser Ser Asp Tyr Tyr Val Lys
            20                  25
```

<210> SEQ ID NO 10
<211> LENGTH: 42
<212> TYPE: PRT
<213> ORGANISM: Artificial Sequence
<220> FEATURE:
<223> OTHER INFORMATION: Synthetic peptide

<400> SEQUENCE: 10

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val
        35                  40

<210> SEQ ID NO 11
<211> LENGTH: 19
<212> TYPE: PRT
<213> ORGANISM: Artificial Sequence
<220> FEATURE:
<223> OTHER INFORMATION: Synthetic peptide

<400> SEQUENCE: 11

His Val Ile Phe Lys Lys Ile Ser Arg Asp Lys Ser Val Thr Ile Tyr
1               5                   10                  15

Leu Gly Asn

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Lys Lys Ile Ser Arg Asp Lys Ser Val Thr Ile
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic peptide

<400> SEQUENCE: 13

Phe Lys Lys Ile Ser Arg Asp Lys Ser Val Thr Ile Tyr
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide

<400> SEQUENCE: 14

Val Ile Phe Lys Lys Ile Ser Arg Asp Lys Ser Val Thr Ile Tyr Leu
1               5                   10                  15

Gly

<210> SEQ ID NO 15
<211> LENGTH: 23
<212> TYPE: PRT

```
<213> ORGANISM: Artificial Sequence
<220> FEATURE:
<223> OTHER INFORMATION: Synthetic peptide

<400> SEQUENCE: 15

Lys Lys Lys Val Ile Phe Lys Lys Ile Ser Arg Asp Lys Ser Val Thr
1               5                   10                  15

Ile Tyr Leu Gly Lys Lys Lys
            20

<210> SEQ ID NO 16
<211> LENGTH: 38
<212> TYPE: PRT
<213> ORGANISM: Artificial Sequence
<220> FEATURE:
<223> OTHER INFORMATION: Synthetic peptide

<400> SEQUENCE: 16

Leu Thr Leu Leu Pro Leu Leu Ala Asn Asn Arg Glu Arg Arg Gly Ile
1               5                   10                  15

Ala Leu Asp Gly Lys Ile Lys His Glu Asp Thr Asn Leu Ala Ser Ser
            20                  25                  30

Thr Ile Ile Lys Glu Gly
        35

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide

<400> SEQUENCE: 17

Asn Arg Glu Arg Arg Gly Ile Ala Leu Asp Gly Lys Ile Lys His Glu
1               5                   10                  15

Asp

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Glu Arg Arg Gly Ile Ala Leu Asp Gly Lys Ile Lys His
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Arg Glu Arg Arg Gly Ile Ala Leu Asp Gly Lys Ile Lys His Glu
1               5                   10                  15

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 20

Asp Gly Lys Ile Lys His Glu Asp Thr Asn Leu Ala Ser Ser Thr Ile
1               5                   10                  15

Ile Lys Glu Gly
            20

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

His Glu Asp Thr Asn Leu Ala Ser Ser Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide

<400> SEQUENCE: 22

Lys His Glu Asp Thr Asn Leu Ala Ser Ser Thr Ile
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Ile Lys His Glu Asp Thr Asn Leu Ala Ser Ser Thr Ile Ile
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Synthetic peptide

<400> SEQUENCE: 24

Lys Ile Lys His Glu Asp Thr Asn Leu Ala Ser Ser Thr Ile Ile Lys
1               5                   10                  15

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide

<400> SEQUENCE: 25

Leu Thr Lys Thr Leu Thr Leu Leu Pro Leu Leu Ala Asn Asn Arg Glu
1               5                   10                  15

Arg Arg

<210> SEQ ID NO 26
<211> LENGTH: 20

```
<212> TYPE: PRT
<213> ORGANISM: Artificial Sequence
<220> FEATURE:
<223> OTHER INFORMATION: Synthetic peptide

<400> SEQUENCE: 26

Leu Thr Leu Leu Pro Leu Leu Ala Asn Asn Arg Glu Arg Arg Gly Ile
1               5                   10                  15

Ala Leu Asp Gly
            20

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide

<400> SEQUENCE: 27

Leu Leu Ala Asn Asn Arg Glu Arg Arg Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide

<400> SEQUENCE: 28

Pro Leu Leu Ala Asn Asn Arg Glu Arg Arg Gly Ile
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic peptide

<400> SEQUENCE: 29

Leu Pro Leu Leu Ala Asn Asn Arg Glu Arg Arg Gly Ile Ala
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Asn Asn Arg Glu Arg Arg Gly Ile Ala Leu Asp Gly Lys Ile Lys
1               5                   10                  15

<210> SEQ ID NO 31
<211> LENGTH: 21
<212> TYPE: PRT
<213> ORGANISM: Artificial Sequence
<220> FEATURE:
<223> OTHER INFORMATION: Synthetic peptide

<400> SEQUENCE: 31

Val Lys Lys Ile Lys Ala Phe Val Glu Gln Val Ala Asn Val Val Leu
1               5                   10                  15

Tyr Ser Ser Asp Tyr
```

```
<210> SEQ ID NO 32
<211> LENGTH: 27
<212> TYPE: PRT
<213> ORGANISM: Artificial Sequence
<220> FEATURE:
<223> OTHER INFORMATION: Synthetic peptide

<400> SEQUENCE: 32

Lys Lys Lys Val Lys Ile Lys Ala Phe Val Glu Gln Val Ala Asn
1               5                   10                  15

Val Val Leu Tyr Ser Ser Asp Tyr Lys Lys Lys
            20                  25

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Ala Phe Val Glu Gln Val Ala Asn Val Val Leu
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Synthetic peptide

<400> SEQUENCE: 34

Lys Lys Lys Ala Phe Val Glu Gln Val Ala Asn Val Val Leu Lys Lys
1               5                   10                  15

Lys

<210> SEQ ID NO 35
<211> LENGTH: 22
<212> TYPE: PRT
<213> ORGANISM: Artificial Sequence
<220> FEATURE:
<223> OTHER INFORMATION: Synthetic peptide

<400> SEQUENCE: 35

Val Ile Gly Leu Thr Phe Arg Arg Asp Leu Tyr Phe Ser Arg Val Gln
1               5                   10                  15

Val Tyr Pro Pro Val Gly
            20

<210> SEQ ID NO 36
<211> LENGTH: 28
<212> TYPE: PRT
<213> ORGANISM: Artificial Sequence
<220> FEATURE:
<223> OTHER INFORMATION: Synthetic peptide

<400> SEQUENCE: 36

Lys Lys Lys Val Ile Gly Leu Thr Phe Arg Arg Asp Leu Tyr Phe Ser
1               5                   10                  15

Arg Val Gln Val Tyr Pro Pro Val Gly Lys Lys Lys
            20                  25
```

```
<210> SEQ ID NO 37
<211> LENGTH: 15
<212> TYPE: PRT
<213> ORGANISM: Artificial Sequence
<220> FEATURE:
<223> OTHER INFORMATION: Synthetic peptide

<400> SEQUENCE: 37

Leu Thr Phe Arg Arg Asp Leu Tyr Phe Ser Arg Val Gln Val Tyr
1               5                   10                  15

<210> SEQ ID NO 38
<211> LENGTH: 21
<212> TYPE: PRT
<213> ORGANISM: Artificial Sequence
<220> FEATURE:
<223> OTHER INFORMATION: Synthetic peptide

<400> SEQUENCE: 38

Lys Lys Lys Leu Thr Phe Arg Arg Asp Leu Tyr Phe Ser Arg Val Gln
1               5                   10                  15

Val Tyr Lys Lys Lys
            20

<210> SEQ ID NO 39
<211> LENGTH: 12
<212> TYPE: PRT
<213> ORGANISM: Artificial Sequence
<220> FEATURE:
<223> OTHER INFORMATION: Synthetic peptide

<400> SEQUENCE: 39

Thr Phe Arg Arg Asp Leu Tyr Phe Ser Arg Val Gln
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic peptide

<400> SEQUENCE: 40

Arg Arg Asp Leu Tyr Phe Ser Arg Val Gln
1               5                   10

<210> SEQ ID NO 41
<211> LENGTH: 25
<212> TYPE: PRT
<213> ORGANISM: Artificial Sequence
<220> FEATURE:
<223> OTHER INFORMATION: Synthetic peptide

<400> SEQUENCE: 41

Ile Asp Arg Thr Val Leu Gly Ile Leu Val Ser Tyr Gln Ile Lys Val
1               5                   10                  15

Lys Leu Thr Val Ser Gly Phe Leu Gly
            20                  25

<210> SEQ ID NO 42
<211> LENGTH: 31
<212> TYPE: PRT
<213> ORGANISM: Artificial Sequence
<220> FEATURE:
<223> OTHER INFORMATION: Synthetic peptide

<400> SEQUENCE: 42
```

```
Lys Lys Lys Ile Asp Arg Thr Val Leu Gly Ile Leu Val Ser Tyr Gln
1               5                   10                  15

Ile Lys Val Lys Leu Thr Val Ser Gly Phe Leu Gly Lys Lys
            20                  25                  30

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Val Leu Gly Ile Leu Val Ser Tyr Gln Ile Lys Val Lys Leu Thr
1               5                   10                  15

<210> SEQ ID NO 44
<211> LENGTH: 21
<212> TYPE: PRT
<213> ORGANISM: Artificial Sequence
<220> FEATURE:
<223> OTHER INFORMATION: Synthetic peptide

<400> SEQUENCE: 44

Lys Lys Lys Val Leu Gly Ile Leu Val Ser Tyr Gln Ile Lys Val Lys
1               5                   10                  15

Leu Thr Lys Lys Lys
            20

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide

<400> SEQUENCE: 45

Gly Ile Leu Val Ser Tyr Gln Ile Lys Val Lys
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Synthetic peptide

<400> SEQUENCE: 46

Lys Lys Lys Gly Ile Leu Val Ser Tyr Gln Ile Lys Val Lys Lys Lys
1               5                   10                  15

Lys

<210> SEQ ID NO 47
<211> LENGTH: 405
<212> TYPE: PRT
<213> ORGANISM: Homo sapiens

<400> SEQUENCE: 47

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
```

```
            35                  40                  45
Val Leu Val Asp Pro Asp Leu Val Lys Gly Lys Val Tyr Val Thr
 50                  55                  60

Leu Thr Cys Ala Phe Arg Tyr Gly Gln Glu Ile Asp Val Ile Gly
 65                  70                  75                  80

Leu Thr Phe Arg Arg Asp Leu Tyr Phe Ser Arg Val Gln Val Tyr Pro
                     85                  90                  95

Pro Val Gly Ala Ala Ser Thr Pro Thr Lys Leu Gln Glu Ser Leu Leu
                    100                 105                 110

Lys Lys Leu Gly Ser Asn Thr Tyr Pro Phe Leu Leu Thr Phe Pro Asp
                    115                 120                 125

Tyr Leu Pro Cys Ser Val Met Leu Gln Pro Ala Pro Gln Asp Ser Gly
                    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Ser Ser Val Arg Leu
                    165                 170                 175

Leu Ile Arg Lys Val Gln His Ala Pro Leu Glu Met Gly Pro Gln Pro
                    180                 185                 190

Arg Ala Glu Ala Ala Trp Gln Phe Phe Met Ser Asp Lys Pro Leu His
                    195                 200                 205

Leu Ala Val Ser Leu Asn Lys Glu Ile Tyr Phe His Gly Glu Pro Ile
                    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                    245                 250                 255

Asp Tyr Tyr Val Lys Pro Val Ala Met Glu Glu Ala Gln Glu Lys Val
                    260                 265                 270

Pro Pro Asn Ser Thr Leu Thr Lys Thr Leu Thr Leu Leu Pro Leu Leu
                    275                 280                 285

Ala Asn Asn Arg Glu Arg Arg Gly Ile Ala Leu Asp Gly Lys Ile Lys
                    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                    325                 330                 335

Leu Thr Val Ser Gly Phe Leu Gly Glu Leu Thr Ser Ser Glu Val Ala
                    340                 345                 350

Thr Glu Val Pro Phe Arg Leu Met His Pro Gln Pro Glu Asp Pro Ala
                    355                 360                 365

Lys Glu Ser Tyr Gln Asp Ala Asn Leu Val Phe Glu Glu Phe Ala Arg
                    370                 375                 380

His Asn Leu Lys Asp Ala Gly Glu Ala Glu Glu Gly Lys Arg Asp Lys
385                 390                 395                 400

Asn Asp Val Asp Glu
                    405
```